United States Patent
Tabak et al.

(10) Patent No.: US 10,937,108 B1
(45) Date of Patent: Mar. 2, 2021

(54) COMPUTER VISION-BASED CLAIMS PROCESSING

(71) Applicant: Pearl Inc., West Hollywood, CA (US)

(72) Inventors: Joshua Alexander Tabak, Los Angeles, CA (US); Adam Michael Wilbert, Los Angeles, CA (US); Mustafa Alammar, Los Angeles, CA (US); Rohit Sanjay Annigeri, Los Angeles, CA (US); Cambron Neil Carter, Los Angeles, CA (US); Ophir Tanz, Los Angeles, CA (US)

(73) Assignee: Pearl Inc., Beverly Hills, CA (US)

( * ) Notice: Subject to any disclaimer, the term of this patent is extended or adjusted under 35 U.S.C. 154(b) by 0 days.

(21) Appl. No.: 17/075,607

(22) Filed: Oct. 20, 2020

Related U.S. Application Data

(60) Provisional application No. 62/962,828, filed on Jan. 17, 2020.

(51) Int. Cl.
| | |
|---|---|
| *G06Q 40/00* | (2012.01) |
| *G06Q 40/08* | (2012.01) |
| *G06F 9/54* | (2006.01) |
| *H04L 9/32* | (2006.01) |
| *G06N 20/00* | (2019.01) |

(52) U.S. Cl.
CPC ............ *G06Q 40/08* (2013.01); *G06F 9/547* (2013.01); *G06N 20/00* (2019.01); *H04L 9/3247* (2013.01)

(58) Field of Classification Search
CPC .................................................... G06Q 40/08
See application file for complete search history.

(56) References Cited

U.S. PATENT DOCUMENTS

| | | | |
|---|---|---|---|
| 5,839,438 | A | 11/1998 | Grattinger et al. |
| 6,409,504 | B1 | 6/2002 | Jones et al. |
| 6,736,776 | B2 | 5/2004 | Miles |
| 7,269,278 | B2 | 9/2007 | Cong et al. |
| 7,421,398 | B2 | 9/2008 | Kimmel |

(Continued)

FOREIGN PATENT DOCUMENTS

| | | |
|---|---|---|
| CA | 2275574 C | 7/2003 |
| CN | 208172859 | 11/2018 |

(Continued)

OTHER PUBLICATIONS

Ahmed, Musheer, "Augmenting Accountability, Security and Fraud Detection in Health Data Sharing Systems", Georgia Institute of Technology, May 2016.

(Continued)

*Primary Examiner* — Edward Chang
(74) *Attorney, Agent, or Firm* — Knobbe, Martens, Olson & Bear, LLP

(57) ABSTRACT

Systems and methods are described for automatically evaluating a claim submitted to an insurance carrier. Claim information and at least one image associated with the claim may be received, where the image has been submitted to a carrier as supporting evidence of a service performed by a submitter of the claim. The system may provide image data and other claim information from the submitted claim as input to machine learning models configured to identify whether the image data, such as a radiograph, supports the other data in the claim submission, such as a treatment code.

19 Claims, 15 Drawing Sheets

(56) References Cited

U.S. PATENT DOCUMENTS

| | | |
|---|---|---|
| 7,472,275 B2 | 12/2008 | Arnouse |
| 7,602,965 B2 | 10/2009 | Hong et al. |
| 7,822,621 B1 | 10/2010 | Chappel |
| 8,417,010 B1 | 4/2013 | Colby |
| 8,463,716 B2 | 6/2013 | Montgomery et al. |
| 8,687,859 B2 | 4/2014 | Yan et al. |
| 8,761,493 B2 | 6/2014 | Chen et al. |
| 8,768,016 B2 | 7/2014 | Pan et al. |
| 8,929,635 B2 | 1/2015 | Chen et al. |
| 9,020,236 B2 | 4/2015 | Wang et al. |
| 9,339,245 B2 | 5/2016 | Colby |
| 9,477,649 B1 | 10/2016 | Davidson et al. |
| 9,839,402 B2 | 12/2017 | Colby |
| 9,886,178 B2 | 2/2018 | Kendall et al. |
| 10,043,073 B2 | 8/2018 | Ross et al. |
| 10,049,457 B2 | 9/2018 | Abraham et al. |
| 10,201,318 B2 | 2/2019 | Tsuji et al. |
| 10,410,363 B2 | 9/2019 | Dekel et al. |
| 10,426,351 B2 | 10/2019 | Abrams et al. |
| 10,722,191 B2 | 7/2020 | Colby |
| 2005/0203777 A1 | 9/2005 | Rosenfeld et al. |
| 2006/0147872 A1 | 7/2006 | Andreiko |
| 2006/0173985 A1 | 8/2006 | Moore |
| 2007/0217648 A1 | 9/2007 | Muehlbauer |
| 2007/0294104 A1 | 12/2007 | Boaz et al. |
| 2009/0076960 A2 | 3/2009 | Hamel et al. |
| 2011/0119088 A1 | 5/2011 | Gunn |
| 2011/0153351 A1 | 6/2011 | Vesper et al. |
| 2012/0148986 A1 | 6/2012 | Yan et al. |
| 2013/0022251 A1 | 1/2013 | Chen et al. |
| 2014/0142984 A1 | 5/2014 | Wright et al. |
| 2014/0149128 A1 | 5/2014 | Getchius |
| 2014/0278529 A1 | 9/2014 | Matos |
| 2014/0314288 A1 | 10/2014 | Roychowdhury et al. |
| 2014/0379361 A1 | 12/2014 | Mahadkar et al. |
| 2015/0046181 A1 | 2/2015 | Adjaoute |
| 2015/0237106 A1 | 8/2015 | Golay |
| 2016/0014288 A1 | 1/2016 | Ono |
| 2016/0038092 A1 | 2/2016 | Golay |
| 2016/0196389 A1 | 7/2016 | Moturu et al. |
| 2017/0053562 A1 | 2/2017 | Bova et al. |
| 2017/0083672 A1 | 3/2017 | Juneau et al. |
| 2017/0161439 A1 | 6/2017 | Raduchel et al. |
| 2018/0122509 A1 | 5/2018 | Christiansson |
| 2018/0174367 A1 | 6/2018 | Marom |
| 2018/0206940 A1 | 7/2018 | Kopelan et al. |
| 2018/0235437 A1 | 8/2018 | Ozerov et al. |
| 2018/0366225 A1 | 12/2018 | Mansi et al. |
| 2019/0066835 A1 | 2/2019 | Lyman et al. |
| 2019/0110753 A1 | 4/2019 | Zhang et al. |
| 2019/0130566 A1 | 5/2019 | Niemeijmer et al. |
| 2019/0313963 A1* | 10/2019 | Hillen .................. G06N 3/0454 |
| 2020/0134823 A1 | 4/2020 | Emoto et al. |
| 2020/0138518 A1 | 5/2020 | Lang |
| 2020/0146646 A1 | 5/2020 | Tuzoff |
| 2020/0305808 A1 | 10/2020 | Ezhov et al. |
| 2020/0381105 A1 | 12/2020 | Bernard et al. |

FOREIGN PATENT DOCUMENTS

| | | |
|---|---|---|
| CN | 109658260 A | 4/2019 |
| EP | 3407229 A1 | 11/2018 |
| EP | 3 503 038 | 6/2019 |
| JP | 2005050246 A1 | 2/2005 |
| KR | 2005020139 A | 3/2005 |
| WO | WO2003071380 A2 | 8/2003 |
| WO | WO2018022705 A1 | 2/2018 |

OTHER PUBLICATIONS

"8 Rules for E-Signature Security", SIGNiX, 2014.
Reducing Healthcare Fraud in Africa; Genkey Solutions b.v., 2016.
McCormick, John, "AI Helps Spot Dental Fraud", Wall Street Journal, Jan. 24, 2020, available at https://www.wsj.com/articles/ai-helps-spot-dental-fraud-11579861801.
Fracaro et al., "The Sensitivity and specificity of Clinical Assessment Compared with Bitewing Radiology for Detection of Occlusal Dentin Caries", American Academy of Pediatric Dentistry 23:3, Mar. 22, 2001, 204-210.
Markowitz et al. "In Vitro Study of the Diagnostic Performance of the Spectra Caries Detention Aid", The Journal of Clinical Dentistry, 2015,17-22,vol. XXXVI No. 1.
Lee et al. "Diagnosis and Prediction of Periodontally Compromised Teeth Using a Deep Learning-Based Convolutional Neural Network Algorithm", Journal of Periodontal & Implant Science, Apr. 23, 2018,114-123.
Lee et al., "Detection and Diagnosis of Dental Caries Using Deep Learning-Based Convolutional Neural Network Algorithm", Journal of Dentistry, Jul. 25, 2018, 106-111, 77.
Hwang et al. "An Overview of Deep Learning in the Field of Dentistry", Image Science in Dentistry, Mar. 25, 2019, 1-7,49.
Murata et al., "Towards a Fully Automated Diagnostic System for Orthodontic Treatment in Dentistry," IEEE Computer Society, 2017, 1-8, 13$^{th}$ international conference on eScience.
Shankeeth et al.,"Automated detection of third molars and mandibular nerve by deep learning" (pp. 1-7), Jun. 21, 2019.
S. B. Kotsiantis, "Supervised Machine Learning: A Review of Classification Techniques", Jul. 16, 2007, Informatica 31 (2007) 249-268.
L. C. Rabelo, A. Jones and Y. Yih, "Development of a real-time learning scheduler using reinforcement learning concepts," 1994.
R. Ho, "Pragmatic Programming Techniques: Characteristics of Machine Learning Model", Feb. 19, 2012, BlogSpot, all pages.
Azmi et al., "Freeman Chain Code Representation in Signature Fraud Detection Based on Nearest Neighbor and ANN Classifiers", 2014.
Calberson et al., "Fraudulent Use of Digital Radiography: Methods to Detect and Protect Digital Radiographs", 2008, JOE, 34(5).
Young-Jun Yu: "Machine Learning for Dental Image Analysis", Nov. 29, 2016, XP055430578, Retrieved from https://arxiv.org/ftp/arxiv/papers/1611/1611.09958.pdf.
Tian Sukun et al: "Automatic Classification and Segmentation of Teeth on 3D Dental Model Using Hierarchical Deep Learning Networks", IEEE ACCESS, vol. 7, Jul. 15, 2019. pp. 84817-84828, XP011734278, D01:10.1109/ACCESS.2019.2924262 [retrieved on Jul. 9, 2019].

* cited by examiner

| Code | ↑ Tooth | Surface | | | | | |
|------|---------|---|---|---|---|---|---|
| D5226 | | | | | | | |
| D5213 | | M | O | D | B | L | |
| D2332 | 10 | M | O | D | B | L | ⚠ Needs Review 402 |
| D7210 | 12 | M | O | D | B | L | |
| D7210 | 13 | M | O | D | B | L | |
| D2392 | 18 | M | O | D | B | L | ⚠ Needs Review |
| D2391 | 18 | M | O | D | B | L | ⚠ Needs Review |
| D2391 | 19 | M | O | D | B | L | |

FIG. 4

| Code | ↑Tooth | Surface | |
|---|---|---|---|
| D5226 | | M O D B L | |
| D5213 | | M O D B L | 502 |
| D2332 | 10 | M O D B L | ⚠ Needs Review / Deny / Approve |
| D7210 | 12 | M O D B L | |
| D7210 | 13 | M O D B L | |
| D2392 | 18 | M O D B L | ⚠ Needs Review |
| D2391 | 18 | M O D B L | ⚠ Needs Review |
| D2391 | 19 | M O D B L | |

FIG. 5

| Code | ↑Tooth | | Surface | | | | |
|---|---|---|---|---|---|---|---|
| D5226 | | 🦷 | M | O | D | B | L | ✓ Approved |
| D5213 | | 🦷 | M | O | D | B | L | ✓ Approved |
| D2332 | 10 | 🦷 | M | O | D | B | L | ⚠ Outside Guidelines |
| D7210 | 12 | 🦷 | M | O | D | B | L | ✓ Approved |
| D7210 | 13 | 🦷 | M | O | D | B | L | ✓ Approved |
| D2392 | 18 | 🦷 | M | O | D | B | L | ⚠ Outside Guidelines |
| D2391 | 18 | 🦷 | M | O | D | B | L | ⚠ Likely Denial |
| D2391 | 19 | 🦷 | M | O | D | B | L | ✓ Approved |

FIG. 6

High Priority

| Claim ID | Provider ID | Provider Score | # Weak Evidence | $USD Weak | # Moderate Evidence | $USD Moderate | $ Total Claim | $ Benefit Remaining | |
|---|---|---|---|---|---|---|---|---|---|
| 10503 | 560 | ★★★★☆ | 1 | $700 | 2 | $250 | $1,350 | $1,500 | Review › |
| 71352 | 501 | ★★★★★ | 3 | $1,000 | 1 | $25 | $1,400 | $1,000 | Review › |
| 03720 | 401 | ★★★★★ | 2 | $600 | 0 | $0 | $1,200 | $957 | Review › |
| 52871 | 437 | ★★★★★ | 1 | $450 | 0 | $0 | $675 | $800 | Review › |

Low Priority

| Claim ID | Provider ID | Provider Score | # Weak Evidence | $USD Weak | # Moderate Evidence | $USD Moderate | $ Total Claim | $ Benefit Remaining | |
|---|---|---|---|---|---|---|---|---|---|
| 67949 | 432 | ★★★★☆ | 0 | $0 | 1 | $250 | $800 | $200 | Review › |
| 28321 | 332 | ★★★★★ | 0 | $0 | 2 | $230 | $776 | $345 | Review › |
| 32387 | 453 | ★★★★☆ | 0 | $0 | 1 | $89 | $450 | $1,500 | Review › |

FIG. 7

| ☆PRESET ▽ | ≡DATA ▽ | ⊙TIME ▽ | ⚲STATUS▽ | | | | | | |
|---|---|---|---|---|---|---|---|---|---|
| ⊗ Patients >1 ⊗ — 902 | | | | | | | | | |
| Group Identifier ↑ | Claims | Patients | Line Items | Unique Codes | Approvals | Denials | Claim Date Range | Most Recent Claim | Status |
| 3600899 | 2 | 2 | 4 | 2 | 4 | 0 | 12 days | Jun 17 2019 | Dismissed |
| 3601440 | 2 | 2 | 6 | 3 | 6 | 0 | 35 days | Apr 16 2019 | Investigation |
| 3601849 | 4 | 2 | 5 | 3 | 5 | 0 | 35 days | Mar 13 2019 | Investigation |
| 3602227 | 2 | 2 | 12 | 7 | 9 | 3 | 0 days | Mar 15 2019 | Investigation |
| 3602469 | 5 | 2 | 10 | 2 | 10 | 0 | 131 days | Jun 5 2018 | Investigation |
| 3604711 | 2 | 2 | 4 | 2 | 4 | 0 | 0 days | Oct 12 2018 | Investigation |
| 3605330 | 4 | 2 | 4 | 1 | 1 | 3 | 132 days | Mar 14 2019 | Investigation |
| 3605500 | 3 | 2 | 8 | 2 | 8 | 0 | 42 days | Oct 30 2018 | Dismissed |

COMPUTER VISION-BASED CLAIMS PROCESSING

PRIORITY AND INCORPORATION BY REFERENCE

Any and all applications for which a foreign or domestic priority claim is identified in the Application Data Sheet as filed with the present application are hereby incorporated by reference under 37 CFR 1.57.

This application claims benefit of U.S. Provisional Patent Application No. 62/962,828, entitled "SYSTEMS AND METHODS FOR INSURANCE FRAUD DETECTION," filed Jan. 17, 2020, which is hereby incorporated by reference in its entirety.

BACKGROUND

A given health insurance carrier, which may also be referred to as an insurance company or insurance provider, may receive thousands of insurance claims each day. Each insurance claim may be provided to the insurance carrier from a healthcare provider (such as a doctor's or dentist's office, a hospital, etc.), where the claim may indicate a healthcare service rendered by the healthcare provider for a patient who is insured by the given insurance carrier. Given the large volume of claims, it would be prohibitively time consuming for carriers to ensure each claim is thoroughly reviewed by experienced examiners. Instead, the majority of claims submitted to many insurance carriers are not fully evaluated for signs of fraud, waste or abuse.

Healthcare providers may commit health insurance fraud in a number of ways. Such fraud may include billing for services or procedures that were never rendered, charging for a more expensive procedure than what was actually performed, falsifying a patient's diagnosis to justify unnecessary tests or procedures, etc. Insurance fraud is a pervasive problem across medicine and dentistry alike. Dental adjudicators review evidence to evaluate medical necessity with the goal of limiting waste and abuse, but suspicious cases often fail to be flagged.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, wherein:

FIGS. 4-7 depict illustrative user interfaces that present information regarding insurance claims and enable a user to make selections, according to some embodiments.

FIG. 9 depicts an illustrative user interface that presents options for grouping insurance claims and viewing associated information.

FIGS. 10 and 11 depict illustrative user interfaces for filtering and reviewing insurance claim information.

FIG. 13 depicts an illustrative user interface for reviewing insurance claims.

DETAILED DESCRIPTION

Figure 1A:
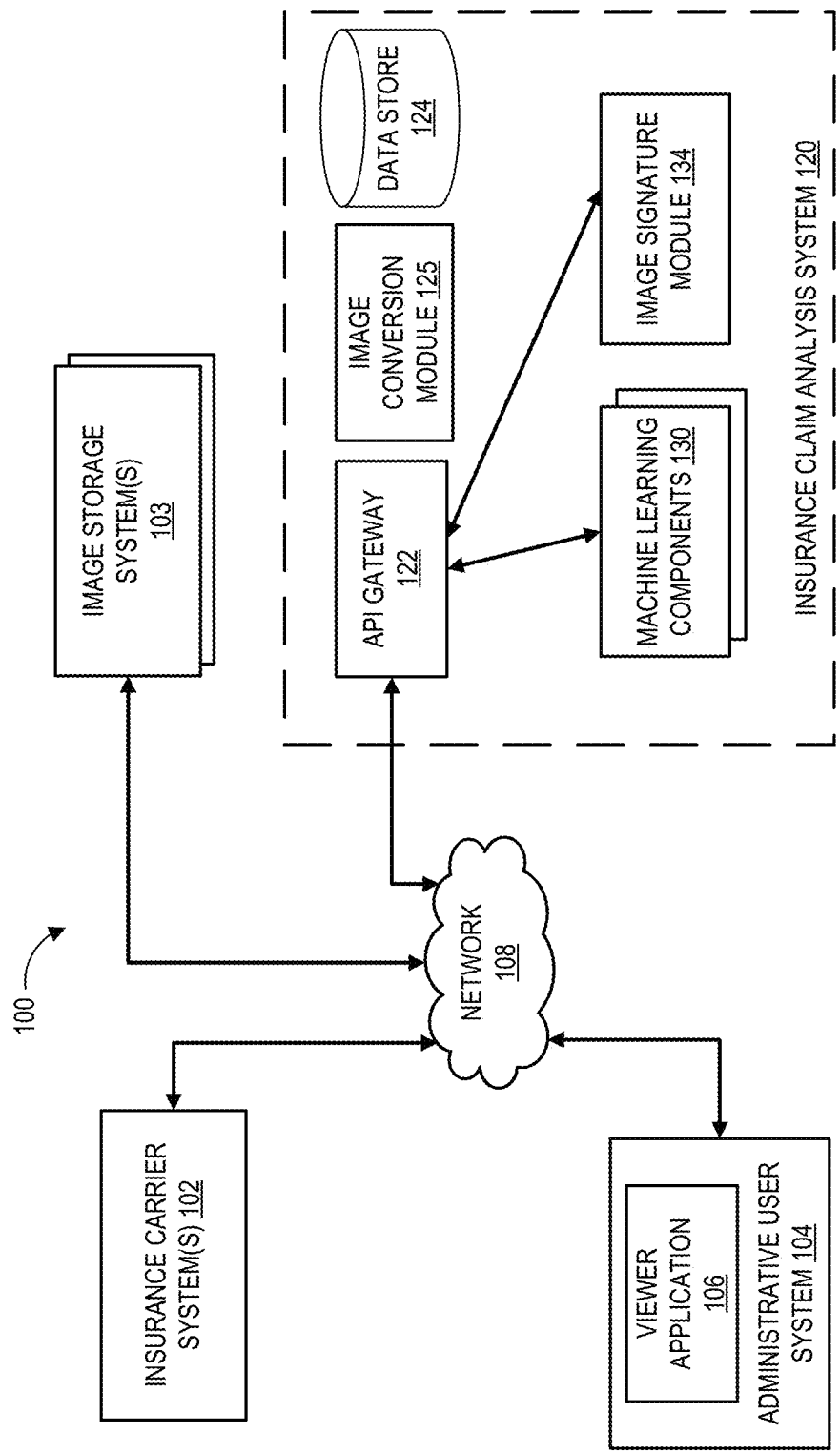
FIG. 1A illustrates a networked computing environment suitable for implementing features of an insurance claim analysis system, according to some embodiments.

Generally described, aspects of the present disclosure relate to computer-implemented processes and system architectures for automatically identifying fraud, waste or abuse in health insurance claims submitted to insurance companies by healthcare providers (such as by hospitals, doctors, dentists, etc.). Health insurance carriers often receive insurance claims (which may refer to requests for reimbursement submitted to the insurance carrier for health services that the submitter provided to a patient insured by the insurance carrier) that are fraudulent or do not represent a real treatment or service that was actually performed on a patient by the provider. The automated methods of fraud, waste and/or abuse detection described herein may replace or supplement manual review by an examiner of an insurance company, as will be further described below. For example, aspects of the present disclosure for enable the focus of an examiner to be directed to the claims with a highest likelihood of fraud. Given that the volume of claims may prohibit manual review of each and every submitted claim (e.g., a majority of claims may be approved without review due to shortage of examiner or other reviewing personnel), ensuring that the claims reviewed are those most likely to have fraud or abuse issues may result in a significantly higher number of fraudulent claims being identified relative to prior art methods. In some embodiments of the present disclosure, certain insurance claims may be automatically approved or denied without manual review based on an automatically determined confidence value, as will be discussed below.

Aspects of the present disclosure relate to machine learning-based approaches to analyzing images that are provided in health insurance reimbursement claims for evidence of insurance fraud. These images may be image files that a healthcare provider attaches or includes in their insurance claim as evidence of the health service that they claim they performed for a patient. In some embodiments, a machine learning model may be trained to learn to detect that a very similar x-ray, radiograph, medical form, doctor's note scan, practice management software screenshot, or other image has been submitted in multiple health insurance claims, which would be a sign of fraud (e.g., a doctor took one radiograph for one patient, but has re-submitted the same radiograph or a modified version of the same radiograph to support a claim for a second patient). A machine learning model may be trained to identify similar images that are not exactly the same, but where it appears that the submitter edited one image to make the second image (e.g., placed a different patient name over the same medical image). As will be further discussed below, the detection of identical images or near-identical images that may be associated with fraudulent claims may be based in part on generating a signature for each image submitted to one or more insurance carriers, such that images likely to be considered nearly identical from a fraud perspective will share the same or similar signature as each other.

In some embodiments, the machine learning approaches to fraud detection discussed herein may further include utilizing computer vision techniques to identify any of various pathologies, conditions, anatomies, anomalies or other medical issues depicted in a radiograph image, such as using systems and methods disclosed in U.S. patent application Ser. No. 16/562,286, entitled SYSTEMS AND METHODS FOR AUTOMATED MEDICAL IMAGE ANALYSIS, filed Sep. 5, 2019 (hereinafter "the '286 application"), the entirety of which is hereby incorporated by reference herein. In some embodiments, the presence of potential fraud, waste or abuse in a claim may be based at least in part on a determination that conditions or features associated with one or more treatment codes submitted in an insurance claim are not identified in the claim's supporting radiograph image(s) using machine learning models such as those disclosed in the '286 application.

Fraud detection solutions described herein may include creating a fingerprint or signature for each claim that enables the system to identify where and when a duplicate or near-duplicate claim was last seen. In some embodiments, by automatically flagging or identifying such similar previously submitted claims, insurance carriers can more easily recognize or be alerted to both clerical errors and potential fraud, waste or abuse present in submitted claims. This may occur as claims are submitted (e.g., before the submitter is reimbursed or paid out by the carrier), or may occur on a batch basis for previously submitted claims as part of an audit or other claim review process.

An example fraudulent claim that may be identified using the systems and methods described herein may be illustrative. As an example, imagine that a dentist or other individual working for a dental practice submits a first insurance claim for reimbursement from a first patient's insurance carrier for a procedure performed for the first patient, where the submission includes supporting imagery that includes a composite image file that depicts eight different sub-images (such as eight different radiographs from a single patient visit, or six radiographs along with two other sub-images of a dentist's notes and other photos or screenshots). The number of images and/or sub-images that the dentist included, in many instances, may not be dictated by the insurance provider, but the imagery may instead be in an unexpected form (from the carrier's perspective) that the dentist chooses to assemble to support the claim.

In the same example scenario, imagine that the same dentist, a month later, submits a second insurance claim for reimbursement for a second procedure purportedly performed after the first procedure above (which may be either for the same patient or a different patient). Consider that the second alleged procedure was a root canal. The dentist may, in fact, have either not actually performed the procedure or may have performed it unnecessarily (such as in a situation where the patient's radiographs and other information would not support performing a root canal under the insurer's reimbursement rules). In such situations, there have been instances where the dentist or other service provider alters a radiograph from the earlier claim submission to add decay or other problems to a tooth (such as a "before" image to support that the tooth required a root canal procedure to be performed) and/or alters a radiograph from the earlier claim submission to show that a root canal had been performed on the tooth (such as an "after" image to support that the root canal procedure was performed by the dentist and should be reimbursed). In other instances, the modifications or alterations to an image may be to text displayed in the image (such as a patient name or date), various image settings (brightness, contrast, etc.), zooming, rotating, cropping, and/or other changes.

The dentist or someone from their staff may have created an image included in the second submission by, for example, cropping the multi-radiograph image from the first submission to only include a blown-up version of a single radiograph, then digitally inserted decay, a root canal, or other issue (such as other pathologies, conditions, anatomies, or anomalies) in an image editing program. Accordingly, a direct comparison of the raw data of the composite image file in the first submission and the cropped, blown-up and altered second image may not indicate a similarity between the files. However, aspects of the present disclosure may automatically extract many sub-images from the first image for separate image signature generation, where one of those signatures (which may be a signature for one of eight or more sub-images in the above example) would be a match or substantial match to the signature generated for the similar image submitted with the second claim submission. As will be further described herein, the systems and methods described herein may identify such a situation as potential or likely fraud, where the two claim submissions may be grouped together automatically for joint review by a user, such as a claims examiner.

FIG. 1A illustrates a networked computing environment 100 suitable for implementing features of an insurance claim analysis system, according to some embodiments. The environment 100 includes a network 108, one or more insurance carrier systems 102, one or more image storage systems 103, an administrative user system 104, and an insurance claim analysis system 120. To simplify discussion and not to limit the present disclosure, FIG. 1A illustrates only one insurance carrier system 102, though multiple insurance carrier systems may be present in many embodiments. For example, the insurance claim analysis system 120 may be configured to provide claim analysis for a number of different insurance carriers, and may identify duplicate claims or other potentially conflicting claims across carriers (e.g., identifying that a claim submitted to a first insurance carrier appears to be potentially fraudulent based on a claim previously submitted to a second insurance carrier).

The administrative user system 104 may be operated by a user associated with either the operator of the insurance claim analysis system 120 or an insurance carrier (such as an operator of the insurance carrier system 102). For example, the viewer application 106 may be installed on one or more computer systems operated by a claims examiner employed by an insurance carrier, where the viewer application may present claim review user interfaces such as those that will be described with respect to FIGS. 4-7 below. In other embodiments, functionality described herein as being provided by the insurance carrier system and the administrative user system may be implemented within a single computing system or device associated with a given insurance carrier.

The insurance claim analysis system 120 can include API gateway 122, one or more data stores 124, an image signature module 134, and machine learning components 130.

The machine learning components may include multiple pre-processing classifiers, machine learning models, and post-processors, such as those further discussed in the '286 application. As will be discussed below, the API gateway 122 can communicate with the systems 102, 103 and/or 104 (e.g., using a network 108, such as the Internet) to receive various information or files (such as claim information, images, etc.) associated with insurance claims and coordinate subsequent image processing and analysis by the machine learning components 130. Although only one network 108 is illustrated, multiple distinct and/or distributed networks may exist. The various systems and other components illustrated in FIG. 1A, including interactions or communications between them, will be described in more detail below with respect to FIG. 1B.

The insurance carrier system 102 illustrated in FIG. 1A may include hardware and software components for establishing communications over a communication network 108. For example, the insurance carrier system 102 may be equipped with networking equipment and network software applications (for example, a web browser and/or a proprietary application or API interface associated with an operator of the insurance claim analysis system 120) that facilitates communications via one or more networks (for example, the Internet, an intranet or a virtual private network). Each insurance carrier system 102 may have varied local computing resources such as central processing units and architectures, memory, mass storage, graphics processing units, communication network availability and bandwidth, and so forth. Further, the insurance carrier system 102 may include any type of computing system. For example, the insurance carrier system 102 may include one or more desktop computers, laptop computers, and/or servers operated in association with a medical practice, in some embodiments. The insurance carrier system 102 can include a data store (not illustrated) that may store various insurance claim information. Such a data store as well as the data store 124 associated with the insurance claim analysis system may employ various security and privacy protocols known in the art for storage of medical data, including Health Insurance Portability and Accountability Act ("HIPAA") compliance.

Figure 1B:
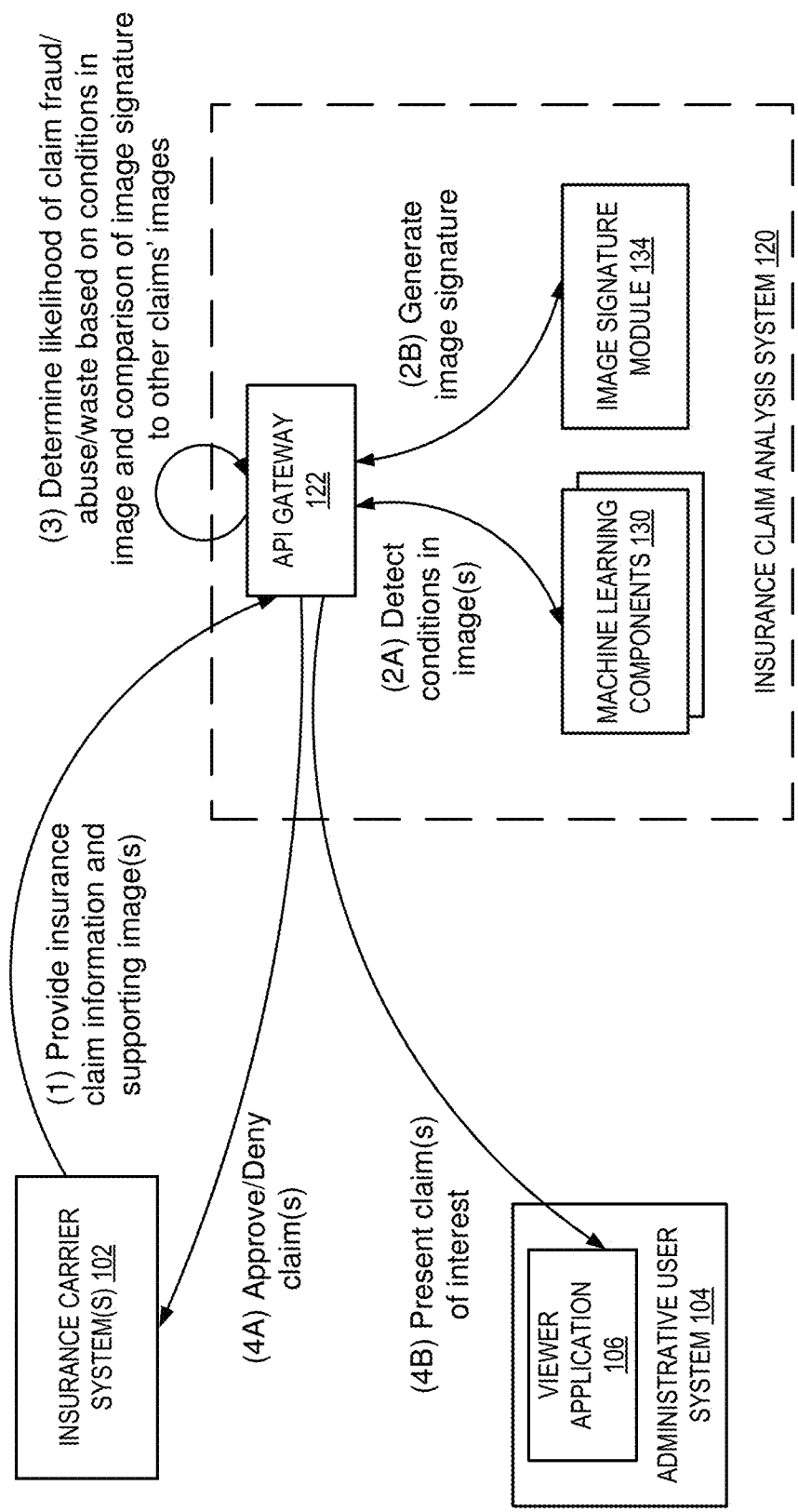
FIG. 1B illustrates example data flow within the networked computing environment of FIG. 1A.

FIG. 1B illustrates example data flow within the networked computing environment of FIG. 1A. For ease of illustration, the data flow of FIG. 1B does not specify whether individual communications between illustrated components or systems are over a network or are local within a single computing system or device. While one example network arrangement is illustrated in FIG. 1A and described above, it will be appreciated that components or subsystems illustrated as part of a single computing system in FIG. 1A may instead be remotely located relative to each other. Similarly, other systems or components illustrated as in network communication with each other in FIG. 1A may in some embodiments be operated together on a single computing system or may be in direct local communication with each other rather than communicating over a network.

The illustrative data flow begins at step (1) with an insurance carrier system 102 providing insurance claim information and supporting image data to the insurance claim analysis system 120, such as via the API gateway 122. For example, the insurance carrier system may send an API request for the insurance claim analysis system 120 to analyze or process one or more insurance claims that have been submitted to the carrier from a healthcare provider. In some instances, a set of claims may be provided in a batch process, while in other instances an individual claim may be sent (e.g., an individual claim may be forwarded to the insurance claim analysis system 120 shortly after or in near real time with respect to a time at which the claim is initially received by the carrier). As discussed above, the claim information may include supporting imagery that a doctor, dentist or other healthcare provider has included with their claim submission to provide evidence or documentation to the carrier of the medical service provided, such as an image file depicting a radiograph, a medical form, a scan of a doctor's note, a practice management software screenshot, or other image.

For each received claim, the API gateway 122 may then provide the corresponding received image(s) and optionally other claim information to both the machine learning components 130 and image signature module 134, which may occur sequentially or in parallel at steps (2A) and (2B). The results of processing the images and other claim information by the machine learning components 130 at step (2A) may result in detection of one or more conditions, diagnoses, or other medical data depicted, present or referenced in the image(s), as will be discussed further below. The image signature module 134 at step (2B) may generate a signature or fingerprint for the image(s) and/or claim as a whole for comparison to signatures or fingerprints from other claims in order to assess potential duplicates or near duplicates, as will be further discussed below. Based on the information determined at steps (2A) and (2B), the API gateway 122 or other component of the insurance claim analysis system 120 may determine a likelihood of claim fraud, waste or abuse at step (3), as will be further discussed with respect to FIG. 3.

For example, the insurance claim analysis system may identify a potential instance of fraud when there is a mismatch between a condition that a doctor indicated was treated or diagnosed as part of a given claim and the machine learning components' assessment of whether that condition is depicted in a supporting radiograph submitted with the claim. As another example, the insurance claim analysis system may identify a potential instance of fraud based on a determination that the image signature generated for an image included with the claim submission matches or is a near match to an image signature of another image previously submitted with one or more prior claims (which may indicate, for example, that a doctor is representing that a given radiograph showing the presence of a given medical condition was captured for a certain patient on a given day, when it was actually a radiograph captured on a different day and/or for a different patient, for which the doctor submitted a separate request for insurance reimbursement).

In some embodiments, the API gateway 122 may then send an API response to the insurance carrier system 102 at step (4A), where the response may include an approval or denial recommendation for the submitted claim(s) based on the assessed likelihood of fraud, waste or abuse. The insurance carrier system 102 may be configured, in some instances, to automatically approve or deny certain claims based on the response (e.g., if the likelihood or score falls above an approval threshold or below a denial threshold, respectively). In some embodiments, the API gateway may, at step (4B), send information to the administrative user system 104 that causes presentation in the viewer application 106 of one or more user interfaces that enable the user (such as an insurance claims examiner) to review and approve/deny individual claims based at least in part on the automated assessment performed by the insurance claim analysis system 120. These and other features of the present disclosure will be further described below with reference to additional figures.

Figure 2:
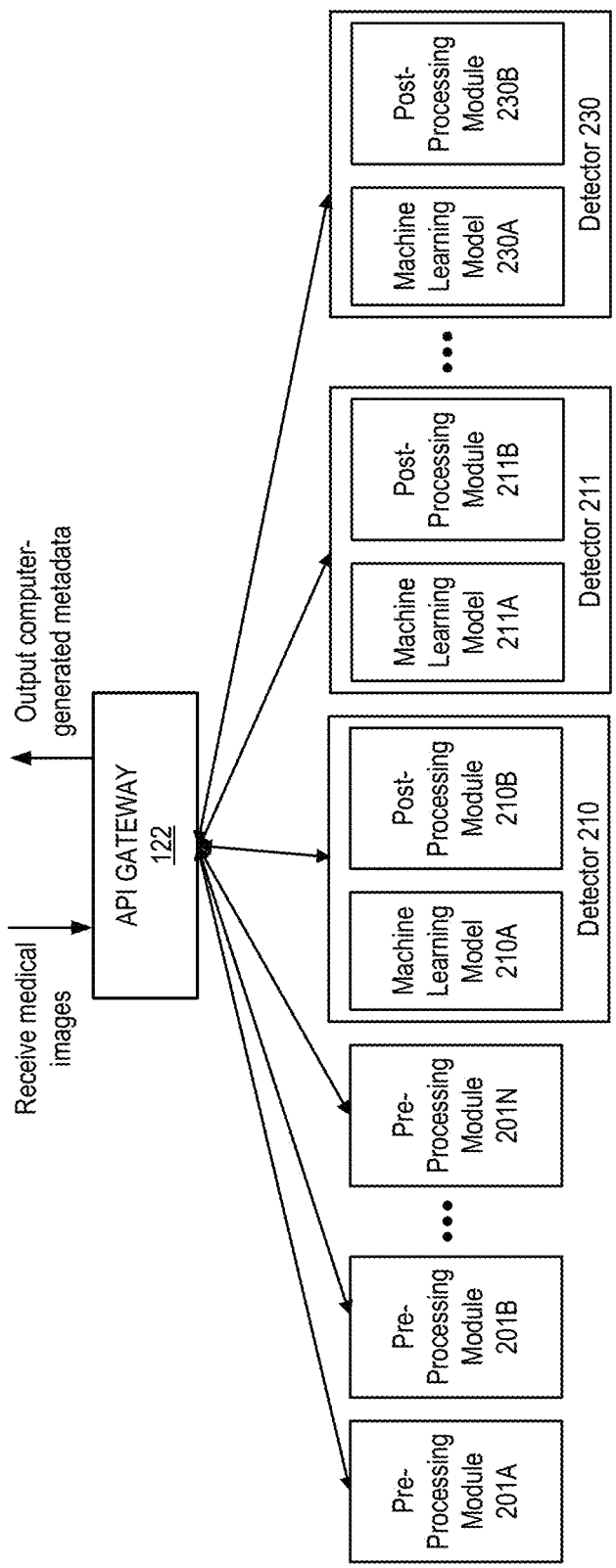
FIG. 2 illustrates a number of different pre-processing modules, machine learning models, and post-processing modules that may be collectively implemented in order to detect different pathologies, anatomies, restorations and/or anomalies depicted in a radiograph.

FIG. 2 illustrates a number of different pre-processing modules, machine learning models, and post-processing modules that may be collectively implemented in order to detect different pathologies, anatomies, restorations, and/or anomalies depicted in a radiograph. The API gateway 122 may generally be responsible for managing calls to various routines and models for generating metadata, such as labels or classifications of pathologies, anatomies, restorations, anomalies, etc., along with optional image annotation data (such as bounding boxes around a given detected pathology, anatomy, etc.). As illustrated, the API gateway 122 makes sequential calls to several pre-processing modules which preprocess the image data, which are shown in FIG. 2 as preprocessing modules 201A, 201B through 201N. It will be appreciated that there may be a large number of pre-processing modules not illustrated.

At least some of the pre-processing modules may generally adjust certain global features in X-rays or other radiograph images by way of image processing. These routines may be configured to enhance and/or standardize the image data before it is processed by machine learning models. One such example of pre-processing is histogram equalization. In some embodiments, the pre-processing modules may include, but are not limited to: (a) a module configured to determine if an image is "whitewashed" such that no image processing techniques (e.g. gamma correction) will sufficiently recover useful information for subsequent processing; (b) a module configured to detect the orientation of the image and adjust the orientation such that subsequent models or modules are only required to handle one orientation; (c) a machine learning model configured to detect teeth or another specific anatomical feature; and/or (d) a machine learning model configured to classify the type of image, such as from possible classifications of panoramic, bitewing, periapical, and/or others. In some embodiments, a pre-processing module may remove or redact personally identifiable information (such as name or patient information) from within images, while in other embodiments the personal information may remain in an image for purposes of image feature input to the machine learning models and/or image signature generation processes with advance approval from the associated carrier (but may then be removed or redacted before image display to any user).

After the pre-processing modules have processed a given image, the API gateway 122 makes parallel calls to a number of different machine learning models (such as machine learning models 210A, 211A, 230A, among others) that have been previously trained to localize and classify (or detect) specific pathologies, anatomies, restorations, and/or anomalies. In doing so, the API gateway may pass forward partial metadata generated from the preprocessing modules, such as preprocessing modules 201A, 201B and 201N. This metadata may then be used by the post-processing routines associated with specific machine learning models, such as post-processing modules 210B, 211B and 230B. As illustrated, each detector 210, 211, 230 and others not illustrated may include both a machine learning model and an associated post-processing module that is specific to the given machine learning model, according to some embodiments.

In some embodiments, each of the specific detectors and/or the associated machine learning model may include one of the following, though others may be implemented or some excluded in other embodiments: a model for detecting the presence of bone loss; a model for detecting the presence of faulty restorations (such as restorations which contain open margins, sub margins, or overhangs); a model for detecting caries; a model for detecting recurrent decay; a model for detecting widened periodontal ligaments; a model for detecting existing restorations (such as crowns, root canals, metal and non-metal fillings, bridges, or implants); a model for detecting potential pathologies (such as cysts, bone lesions, cancerous growths or malignancies); a model to detect calculus; a model to detect existing anatomy (such as sinuses, nerves, nasal canals, orbits, or zygomas); a model to detect teeth by number; a model to detect crowns and roots of teeth; a model to detect the size of the airway; a model to detect quantity and quality of dental implant site; a model to detect third molar impaction; a model to detect jaw fractures; a model to detect facial trauma; a model to detect arch forms of jaws; and/or a model to detect orthodontic cephalometric tracings. In some embodiments, a single model may be trained to identify a large set of the above or all of the above, in addition to individual models that detect individual conditions above.

In some embodiments, both a first model and a second model may each individually be configured to detect multiple pathologies that are the same between the two models, but the models may have been trained using different machine learning algorithms. For example, two models employing different machine learning algorithms may each be trained to classify image data as depicting any of the same list of pathologies (such as twenty different pathologies), but may output different classification results for the same input images based on differences in the respective models' training data and/or specific machine learning algorithm or structure used for the particular model. In such embodiments in which two or more machine learning models may be trained to detect the same or overlapping sets of potential pathologies, the system 120 may be configured to apply a voting methodology or other resolution process to determine an ultimate classification result based on collective output of the models. It will be appreciated that many known methods of ensemble learning may be used in embodiments in which multiple alternative models are trained to make similar classification predictions using different supervised and/or unsupervised machine learning techniques. As discussed above, other models may be specific to individual pathologies (such as a model trained to detect only a single pathology as opposed to any of a set of pathology classes or labels).

As discussed further in the '286 application, training of the various machine learning models may include data collection by way of individual annotation and/or consensus-based annotation. Consensus may be arrived at programmatically in some embodiments, such as based on a Jaccard index being determined to be at or above a given threshold between two individual annotations. Consensus annotation may additionally or alternatively come from annotators directly working together to jointly annotate radiographs together. Once the data has reached an acceptable volume and variance (such as with respect to pre-defined feature spaces) it may be used to train the models and may additionally be used for measuring accuracy of the trained models.

The machine learning architectures used for training may include various forms of neural networks, deep learning models, and/or other architectures for accomplishing classification and/or localization via supervised and/or unsupervised learning. In some embodiments, the specific architectures may be selected to achieve two goals: (1) to localize regions in a radiograph which contain features of interest and (2) to classify each of said regions. The final output in most instances will be some number of predicted regions along with associated probabilities of said regions containing a particular pathology, restoration, anatomy, or anomaly of interest. As non-limiting examples according to some embodiments, one or more of the models may resemble or include single shot detector (SSD), faster region-based convolutional neural networks (Faster R-CNN), "You Only Look Once" (YOLO) real-time object detection, and/or a U-Net convolutional neural network. It will be appreciated that various other existing or future object detection, localization, and/or classification methodologies may be used for individual models, and that different models within a single embodiment may use different training methodologies and/or machine learning architectures.

As shown in FIG. 2, each machine learning model (such as machine learning model 210A) is coupled with a model-specific post-processing module (such as post-processing module 210B). Post-processing modules may merge, edit, and/or augment the produced metadata based on algorithmically combining output from machine learning models. One such example is reducing false positives in anatomical regions in which the predicted property is known never to exist. The functionality implemented by a given post-processing module may vary based on what the associated machine learning model is designed to localize and classify. For example, if machine learning model 211A is configured to classify caries (which can only exist on teeth), the combination of this caries detection model and a tooth detection pre-processing module may be used by the post-processing module 211B to confirm that the machine learning model 211A did not classify a region as caries if the region was not also classified as a tooth in pre-processing.

In some embodiments, certain machine learning models or detectors may produce metadata that is used by a subsequent detector or machine learning model. For example, in one embodiment, detector 211 may be a sub-detector of detector 210. For example, detector 210 may localize a region in the image which has been predicted to contain a specific pathology, anatomy, restoration and/or anomaly. Then, detector 211 may take this metadata as input and restrict its processing to only those regions of interest to it. As a more specific example, detector 210 may predict the presence of caries. Detector 211 may crop only those regions containing caries (as predicted by detector 210), then detector 211 may classify only those regions for the particular type of carie (e.g. into dentin, into enamel, or into pulp). In some embodiments, there may be more than one sub-detector for a given detector. For example, following the example above, there may also be a sub-detector to classify detected carie regions into differing categories, such as gross, mesial, occlusal/incisal, distal, facial, lingual/palatal, incipient, or recurrent. Once all detectors have generated their respective metadata, the API gateway 122 may construct or generate a final output message or metadata set that is passed back as the final response back to a requester, which may be another component within the system 120 or an external system, such as an insurance carrier system or viewer application.

Figure 3:
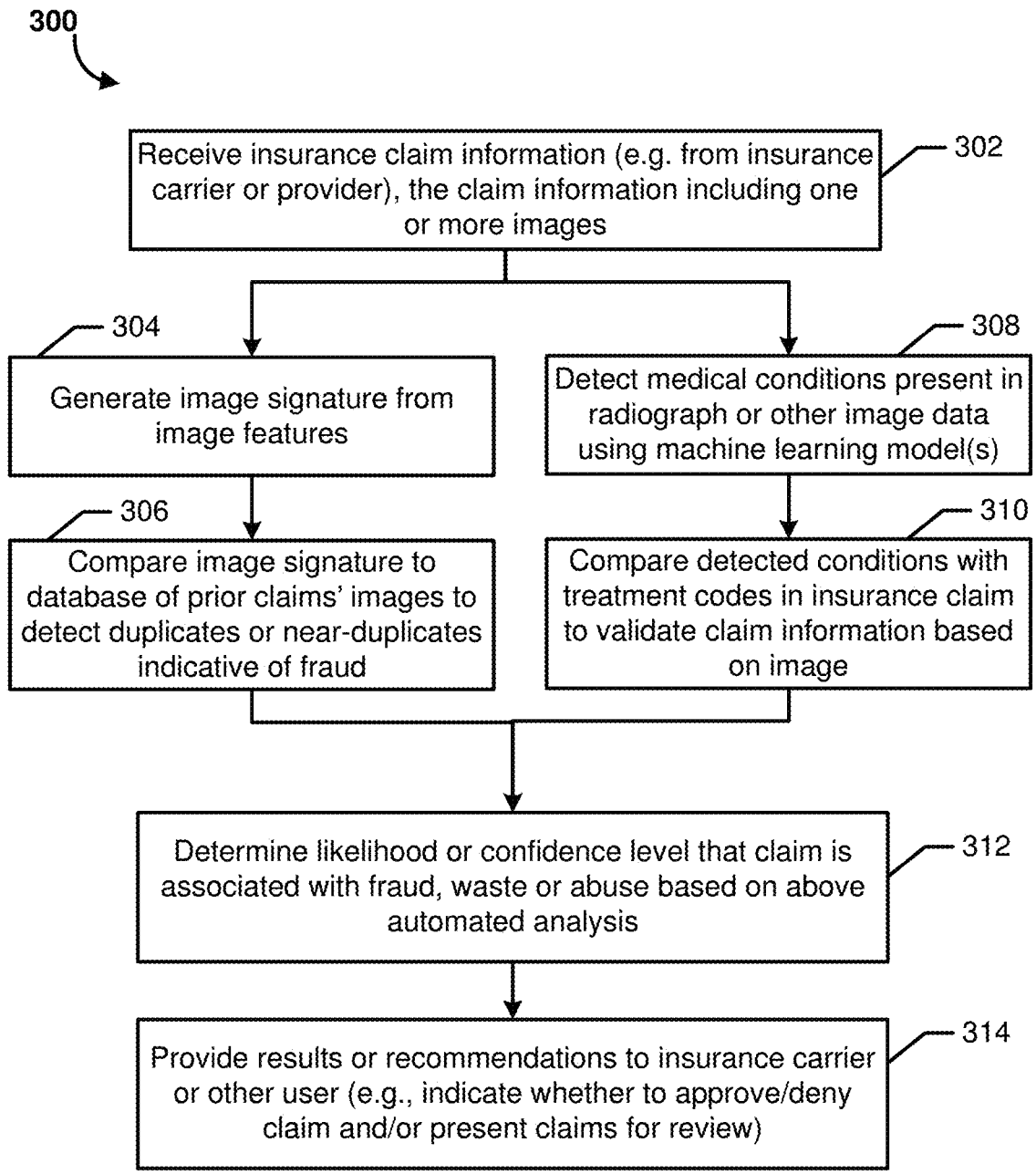
FIG. 3 is a flow diagram of an illustrative method for detecting a potentially fraudulent insurance claim, according to some embodiments.

FIG. 3 is a flow diagram of an illustrative method 300 for detecting a potentially fraudulent insurance claim, or an insurance claim with other signs of waste or abuse, according to some embodiments. The illustrative method 300 may be performed by the insurance claim analysis system 120, in some embodiments.

The illustrative method 300 begins at block 302, where the insurance claim analysis system 120 may receive insurance claim information, such as from insurance carrier system. As discussed above, the claim information may include one or more images, such as digital image files that depict radiographs, doctor's notes (e.g., a photograph or scan of a doctor's handwritten notes, or a screenshot of digitally written notes), practice management software application screenshots or exports (e.g., an export in an image file format or PDF format), prescriptions, patient charts, test results, filled in medical forms, and/or other visual imagery. The claim information received or obtained at block 302 may further include various claim information or metadata, which may be in a structured form (e.g., field names and corresponding values or entries). Such claim information may include, for example, patient data, a unique identifier for the claim, one or more treatment codes, healthcare provider information, time and date information, and/or other data known in the field of insurance claim processing.

The method 300 may then proceed to blocks 304 and/or to block 308 to begin analysis of the claim information and image(s). While block 304 is implemented prior to block 306, and block 308 is implemented prior to block 310, the pair of blocks 304 and 306 may be implemented either before, after or in parallel with the pair of blocks 308 and 310. In some embodiments, the likelihood of fraud (determined at block 312 discussed below) may be based on results of only one of the blocks 306 or 310 (e.g., based only on image signature comparisons or only on medical condition analysis), or may be based on both. Thus, it will be appreciated that there are embodiments in which blocks 304 and 306 may not be implemented, and other embodiments in which blocks 308 and 310 may not be implemented.

At block 304, the insurance claim analysis system 120 may generate an image signature (which may be considered an image fingerprint in some embodiments) for either each individual image associated with the claim or for a set of images associated with the claim. In some embodiments, this may first include pre-processing composite imagery, such as using a machine learning model to extract relevant child images if multiple are present in a parent image. The insurance claim analysis system 120 may generate or extract features for the image(s) using one or more previously trained machine learning models (training will be further discussed below). The features may generally be extracted using mathematical transformations of the image data and/or as the features determined at one or more layers of a machine learning model. Additional details regarding such transformations and machine learning models will be further discussed below. The signature(s) may then be stored in a database for future comparisons to images associated with other insurance claims.

Next, at block 306, the insurance claim analysis system 120 may compare the generated image signature(s) for the currently analyzed claim to a database of prior claims' images to detect duplicates or near-duplicates indicative of fraud. As will be further discussed below, the signatures may be generated in manner whereby an image that has been modified so as not to appear identical to a prior image (e.g., a radiograph, prescription, etc. in which an original patient name has been changed or an image has been cropped or rotated) will nonetheless have a matching or close signature to the prior image (e.g. based on Euclidian distance between the signatures, in one embodiment). If duplicate or near duplicate images are found for the currently analyzed image in the database of claims, the system may flag the relevant image and/or claim as potentially fraudulent.

At block 308 (which may be performed before or after blocks 304 and/or 306, as discussed above), the insurance claim analysis system 120 may detect one or more pathologies, conditions, anatomies, anomalies or other medical issues depicted in a radiograph image, such as using machine learning systems and methods disclosed in the '286 application referenced above. At block 310, the insurance claim analysis system 120 may compare the detected condition(s) or other medical issue(s) depicted in the radiograph image with one or more treatment codes that were submitted in the claim information. This may include consulting a lookup table or mapping data that maps treatment codes to classification labels that the machine learning models are configured to predict from radiograph image data. The presence of potential fraud may be flagged by the system if the conditions or features associated with one or more treatment codes submitted in an insurance claim are not identified in the claim's supporting radiograph image(s) using machine learning models such as those disclosed in the '286 application.

For example, if a dentist submits an insurance claim containing a treatment code for a root canal, but the machine learning model does not identify the presence of a root canal in the supporting radiograph provided by the dentist to the insurance carrier, the system may flag the claim for further review by a claims examiner. An example in which the system may recommend approval of a claim may be (assuming that no duplicate image signatures were found) that an instance of caries (approaching or into pulp) was detected by the machine learning model(s) and the claim includes a treatment code for crown installation, which the system may be configured to recognize is an appropriate mapping between treatment code and radiograph condition.

In some embodiments, the comparison of the detected conditions with the treatment code to validate the claim information (at block 310) and/or an associated decision whether to automatically approve or deny the claim may be based in part on a stored rule set, logic or code module(s) specific to a given insurance carrier that received the insurance claim submission for reimbursement. For example, as will be further described below, the insurance claim analysis system 120 may employ logic such as that illustrated as a sample in FIG. 14 along with the machine learning output in order to determine whether the imagery submitted with a claim submission should lead to approval or denial of the claim. For example, an insurance carrier that handles Medicare claims may have different acceptance criteria than a high value private carrier. As a specific example, if a machine learning model described herein identifies that a radiograph shows 5 mm of bone loss on a tooth, that may pass a bone loss threshold (e.g., a 4.5 mm threshold) set by one insurance carrier as sufficient bone loss for the carrier to reimburse for a crown procedure, whereas the same 5 mm bone loss may not meet a different bone loss threshold (e.g., a 6 mm threshold) set by a second insurance carrier as sufficient bone loss for the second carrier to reimburse for a crown procedure. Thus, the same ground truth output of the machine learning model(s) may lead to different approval or denial decisions for an insurance claim depending on the carrier-specific rules or heuristics applied for a particular carrier. It will be appreciated that these heuristics or rules for automated approval or denial of a claim may be stored in various forms, such as executable code, a JavaScript Object Notation (JSON) or similar format file, an XML file, and/or in other manners.

The rules or heuristics for a given carrier may be a combination of imagery-based rules (e.g., conditions that may be identified from radiographs) and patient history-based rules (e.g., whether or not the patient had certain conditions or procedures in some previous time period, such as the past six months, as determined from metadata, doctors' notes, electronic health record data, practice management software screenshots, and/or other data supporting a claim, patient record or past claims).

At block 312, the insurance claim analysis system 120 may determine a likelihood or confidence level (such as a numeric score) that the analyzed claim is associated with fraud, waste or abuse based on the above-discussed automated analysis of blocks 306 and/or 310. In other instances, the confidence level may additionally or alternatively represent whether the claim should be approved or denied by the carrier, which may be based on criteria other than whether there are indicia of fraud, waste or abuse (e.g., radiographs and/or other supporting data for the claim may indicate that a treatment or service performed by the provider was not warranted by the patient's condition or is not eligible for insurance coverage in the particular circumstances, which may be based on carrier-specific rules). This likelihood, confidence level or score may be determined in a number of ways depending on the embodiment. For example, certain flagged instances discussed above may lead to an automatic classification of potential fraud (e.g., a high likelihood or score). In other embodiments, various weights may be assigned to different factors, rules may be applied, and/or machine learning models may be trained to generate the likelihood of fraud from the various information and comparisons discussed above. At block 314, the results of the analysis may be used to generate recommendations to a user of whether to approve or deny the claim, generate an automated approval or denial, and/or present claims to a user for review. Recognized relationships between different claims (e.g. relationships between claims having signature similarity and/or various other associated metadata in common) may also be stored in the claim database to group sets of claims that follow patterns of similarity or that are likely to include one or more fraudulent claims in view of one another. Example claim review user interfaces will be discussed below with respect to FIGS. 4-7.

Certain methods for image signature generation will now be described with respect to certain embodiments, but are not intended to be limited. As mentioned above, the signature for an image may be generated based on extracted features of the image, where the extracted features may be based on mathematical transformation of the image data and/or may be the features generated at one or more layers of a machine learning model. In some embodiments, feature extraction may include methods such as scale and rotation-invariant descriptors (e.g., SURF, PHOG, GLOH, etc.). In some embodiments, the features for generating a signature may be based on feature maps from one of more convolutional layers in a convolutional neural network (e.g., VGG-16, ResNet, DenseNet, an encoder branch of Autoencoder, etc.), which may rely on supervised or unsupervised learning. Transformations applied may include subsampling of raw image intensities, and/or re-representation of the image by one or more transformations (such as the Discrete Cosine Transform (DCT)).

In some embodiments, the machine learning model(s), such as a convolutional neural network, employed in the feature extraction process may be trained on general imagery, trained on claim-specific imagery, and/or trained on artificially generated near-duplicates that are generated based on transformations known to be present prior instances of fraud, waste or abuse of insurance claims. In embodiments in which artificially generated near-duplicates are employed in training, these near duplicates may be created from base images by applying one or more transformations such as versions of the following that are consistent with prior instances of fraud, waste or abuse: rotation, illumination perturbations, insertion or removal of text, image superimposition, cropping, and/or other transformation found to commonly occur in instances of fraudulent or near duplicate claim submissions.

Once the extracted features are determined for an image, the signature may be generated, in some embodiments, using a hashing function. For example, a hashing function may be used to compress the image features into a fixed-length signature or hash (which may be considered feature hashing). The feature hashing may include calculating the average feature and then thresholding each feature element by its proximity to the average. As another example, the feature hashing may include assigning a hash value per element using the sign of the feature (e.g. 0 for negative, 1 for positive). However, it will be appreciated by one of ordinary skill in the art that any of a wide variety of hashing methods or other algorithms may be employed to generate the signature from the extracted image features.

FIGS. 4-7 depict illustrative user interfaces that present information regarding insurance claims and enable a user to make selections, according to some embodiments. The user may be, for example, an insurance claims examiner, clinician or auditor, in some instances. The user interfaces may be presented for display, in some embodiments, by the viewer application 106 of the administrative user system 104 based in part on information generated by the insurance claim analysis system 120.

As illustrated in FIG. 4, the user interface 400 may be considered an example claims approval interface. The displayed rows may each correspond to a different claim that has been submitted for approval. The "code" column may include a code value that is part of the claim as originally assigned by the insurance carrier, for instance. The "tooth" column may include a tooth number that was output by the machine learning models discussed above (such as those in the '286 application) based on tooth detection performed on a radiograph image, for instance. The "tooth" column entry, in other embodiments, may additionally or alternatively be populated based on claim information, such as claim information received from the insurance carrier. The user may select the image icons in the next column to view the corresponding image. The icons in the "surface" column may be additional information from the insurance claim. The claim data that the insurance claim analysis system 120 has flagged as needing review (e.g., items potentially associated with fraud, waste or abuse) include a "needs review" selectable option, such as option 402. If the user selects option 402, the user interface display may be updated as shown in user interface 500 of FIG. 5 to include drop-down options to approve or deny the claim (as shown at 502). FIG. 6 then illustrates an interface displaying the status of a number of claims as "approved" and another as "likely denial." These statuses may have been automatically applied by the insurance claim analysis system 120 in some embodiments, or may have been the result of manual selection by the user.

Other user interfaces similar to those described above may further include functionality for the user to enter various forms of claim queries, flag images or claims, and/or bookmark images or claims. In some embodiments, the user may toggle between browse or query modes, where a query mode may enable the user to enter queries to search the claim database (such as using SQL or similar commands). For example, the user may be able to search for all matches for a particular image signature (e.g., see that a given image has been submitted in duplicate or near duplicate form across ten different claims), filter or sort the displayed claims by treatment code or other field, etc.

FIG. 7 illustrates an example user interface for claim triaging in which a user may quickly separate claims for review into high and low priority based on the automated assessments made by the insurance claim analysis system 120. For example, the claims may be automatically ranked or sorted based on their predicted likelihood of denial (such as due to potential fraud, waste or abuse) as determined by the insurance claim analysis system 120. As illustrated, the displayed information for the high priority claims may include data such as the number of instances of weak evidence and the total dollars associated with the weak evidence. In this manner, if the user only has time to manually review a small subset of the total claims that have been submitted, the user may focus on the high value claims to lower the carrier's potential losses relative to including these high value claims in an auto-approved bucket (as may occur in prior art methods).

Figure 8:
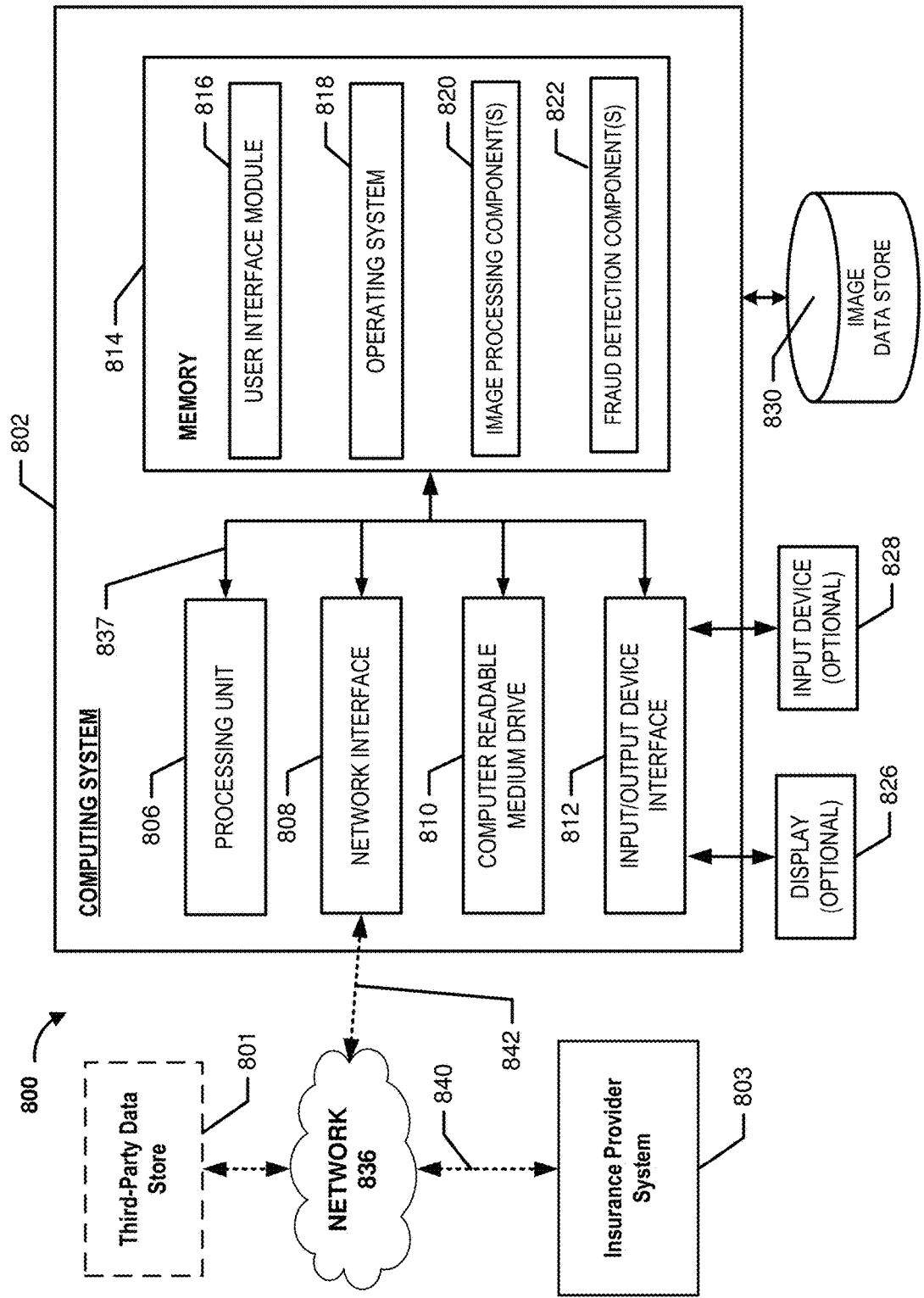
FIG. 8 is a system block diagram of a computing environment suitable for use in various embodiments of the present disclosure.

FIG. 8 illustrates a general architecture of a computing environment 800, according to some embodiments. As depicted in FIG. 8, the computing environment 800 may include a computing system 802. The general architecture of the computing system 802 may include an arrangement of computer hardware and software components used to implement aspects of the present disclosure. The computing system 802 may include many more (or fewer) elements than those shown in FIG. 8. It is not necessary, however, that all of these generally conventional elements be shown in order to provide an enabling disclosure. In some embodiments, the computing system 802 may be an example of what is referred to as the insurance claim system above, though an insurance carrier system and/or administrative user system described above may include one or more similar components, in some embodiments.

As illustrated, the computing system 802 includes a processing unit 806, a network interface 808, a computer readable medium drive 810, an input/output device interface 812, an optional display 826, and an optional input device 828, all of which may communicate with one another by way of a communication bus 837. The processing unit 806 may communicate to and from memory 814 and may provide output information for the optional display 826 via the input/output device interface 812. The input/output device interface 812 may also accept input from the optional input device 828, such as a keyboard, mouse, digital pen, microphone, touch screen, gesture recognition system, voice recognition system, or other input device known in the art.

The memory 814 may contain computer program instructions (grouped as modules or components in some embodiments) that the processing unit 806 may execute in order to implement one or more embodiments described herein. The memory 814 may generally include RAM, ROM and/or other persistent, auxiliary or non-transitory computer-readable media. The memory 814 may store an operating system 818 that provides computer program instructions for use by the processing unit 806 in the general administration and operation of the computing system 802. The memory 814 may further include computer program instructions and other information for implementing aspects of the present disclosure. For example, in one embodiment, the memory 814 may include a user interface module 816 that generates user interfaces (and/or instructions therefor) for display upon a computing system, e.g., via a navigation interface such as a browser or application installed on the computing system 802 or the client computing system 803.

In some embodiments, the memory 814 may include one or more image processing components 820 and fraud detection components 822, which may be executed by the processing unit 806 to perform operations according to various embodiments described herein. The modules 820 and/or 822 may access the image data store 830 in order to retrieve and analyze image data and generate other associated data as described herein. Other data stores, such as a claims data store, may also be present in some embodiments. The data store(s) may be part of the computing system 802, remote from the computing system 802, and/or may be a network-based service.

In some embodiments, the network interface 808 may provide connectivity to one or more networks or computing systems, and the processing unit 806 may receive information and instructions from other computing systems or services via one or more networks. In the example illustrated in FIG. 8, the network interface 808 may be in communication with an insurance provider system 803 via the network 836, such as the Internet. In particular, the computing system 802 may establish a communication link 842 with a network 836 (e.g., using known protocols) in order to send communications to the computing system 803 over the network 836. Similarly, the computing system 803 may send communications to the computing system 802 over the network 836 via a wired or wireless communication link 840. In some embodiments, the computing system 802 may additionally communicate via the network 836 with an optional third-party data store or data service 801, which may be used by the computing system 802 to retrieve remotely stored image files, claims data, and/or other information, data or files. The computing systems 802 and 803 may be any of a number of computing systems including, but not limited to, a laptop, a personal computer, a mobile phone, a smartphone, a tablet computer, another wireless device, a set-top or other television box, one or more servers, and the like. The system 803 may include similar hardware to that illustrated as being included in computing system 802, such as a display, processing unit, network interface, memory, operating system, etc.

As will be further described below with respect to user interfaces illustrated in FIGS. 9-11 and 13, systems and methods described herein include grouping insurance claims that are joined by their associated image signatures, and enabling a user to review the claim information as a claim group. These interfaces include the ability for the user to view individual claim imagery accessed from within a group view interface. Thus, insurance claims that the system has automatically grouped together (or otherwise linked or associated with each other based on machine learning analysis and/or image signatures discussed above) may be viewed by the user in parallel to facilitate visual inspection by the user to determine whether potential fraud or other issues exist (such as fraud, waste or abuse of insurance reimbursement policies of an insurance carrier for which the user works or is associated). Claims data, including at the group level, may be rank ordered based on potential for fraud, waste and/or abuse, as determined by the insurance claim analysis system 120, such as to direct a user's attention to the most likely instances of fraud during a user's review of a user interface that presents claims data.

As shown in the user interfaces further described below, various claim views and associated features may be provided to a user. For example, a user interface displaying various grouped claim information may enable toggling which claims are to be viewed (either at the group level or within a group). The user interfaces may further enable a user to select to apply a filter (such as by selecting an operator from a list including less than, less than or equal, equal to, greater than, greater than equal to, etc.) to groups of claims based on predefined criteria. The predefined criteria for a group that may be selected and an associated operator applied to may include one or more of the following, in one embodiment: number of unique patients in the group, number of unique claims in the group, time disparity between claims belonging to the group, a particular time period (such as may be defined by day, week, month, year, etc.), and/or number of unique treatment codes in the group. A user may save custom combinations of any search or filter criteria for quick access and execution in the future with respect to updated claims data.

As will be further discussed below, user interfaces described herein may enable a user to flag a claim group for further review (such as be selecting an option reading "Requires investigation") or as dismissed upon manual review (where dismissed may represent that the user has determined that the claim(s) do not rise to a level of fraud that should be further pursued, or are a false positive identified by the system's automated processes). The user may organize large amounts of claim groups into bins, thus providing at least two levels of categorization or aggregation among related claims (e.g., the system may automatically create groups of claims based on image analysis and machine learning features described above, and the user may then combine groups of claims into bins or other higher level groupings).

Once groups and/or bins are created, new incoming claims data may be automatically analyzed by the system to determine the likelihood that an incoming claim is fraudulent (or has waste or abuse issues) as well as to determine which group(s) each incoming claim should be assigned by the system. A user may review and adjust the rules, functions, and/or criteria that govern the grouping logic, such that new groups may be realized and generated with respect to existing or future claims data. These and other automated features (such as claim analysis, grouping, cataloging in the database, etc.) may be initiated, in some embodiments, via an API (such as API gateway 122) that an insurance company client system calls to send claim information on an individual claim basis or batch basis to the insurance claim analysis system 120.

FIG. 9 depicts an illustrative user interface 900 that presents options for grouping insurance claims and viewing associated information. The user interfaces in FIGS. 9-13 may be presented for display, in some embodiments, by the viewer application 106 of the administrative user system 104 based in part on information generated by the insurance claim analysis system 120. User interface 900 may be presented to a user who has requested to review groups of claims, where each group is identified by a "group identifier." In this instance, claims have been grouped with one another (and assigned the same group identifier as one another) if they include at least one matching image signature. Each group may generally include two or more claims, which may relate to one or more patients.

In user interface 900, the user has selected a filter option 902 indicating that only groups relating to two or more patients should be displayed (e.g., a claim group will not be displayed if all of its claims relate to the same patient as one another). The user may choose other filter options, in some embodiments, such as to filter based on various types of data present in the claim groups, a specific time period (e.g., claims submitted over a week, month, year, etc.), a claims status, and/or other criteria. Date related filters or criteria that may be set by a user may include an amount of time separating claims of the group (such as indicating that groups should only be shown where there are more than 30 days between the service dates of individual claims in the group). The user may also select a sort order, such as by selecting any of the table headings (as illustrated, the current sort order is by group identifier number). A user may save a given combination of grouping criteria and/or filter information as a preset, which may later be selected by the user in the future to review claim groups for other data sets.

As further shown in user interface 900, the user may view and/or change an entry in the "status" column for individual claim groups. In the illustrated embodiment, status for a given claim group may be "dismissed" or "investigation." The "dismissed" status may indicate that a user has determined that the group is not an example of fraud, waste or abuse. For example, the dismissed status may indicate that the user has determined no further review of the group is needed with respect to fraud, waste or abuse, which may occur in association with a false positive result of the machine learning models' fraud analysis or when a clerical error was present. The "investigation" status may be selected by a user to indicate to one or more other individuals associated with the given carrier that a particular group of claims should be further reviewed in association with fraud or abuse, such as for the carrier to decide whether to litigate one or more claims by initiating a legal suit.

Figure 10:
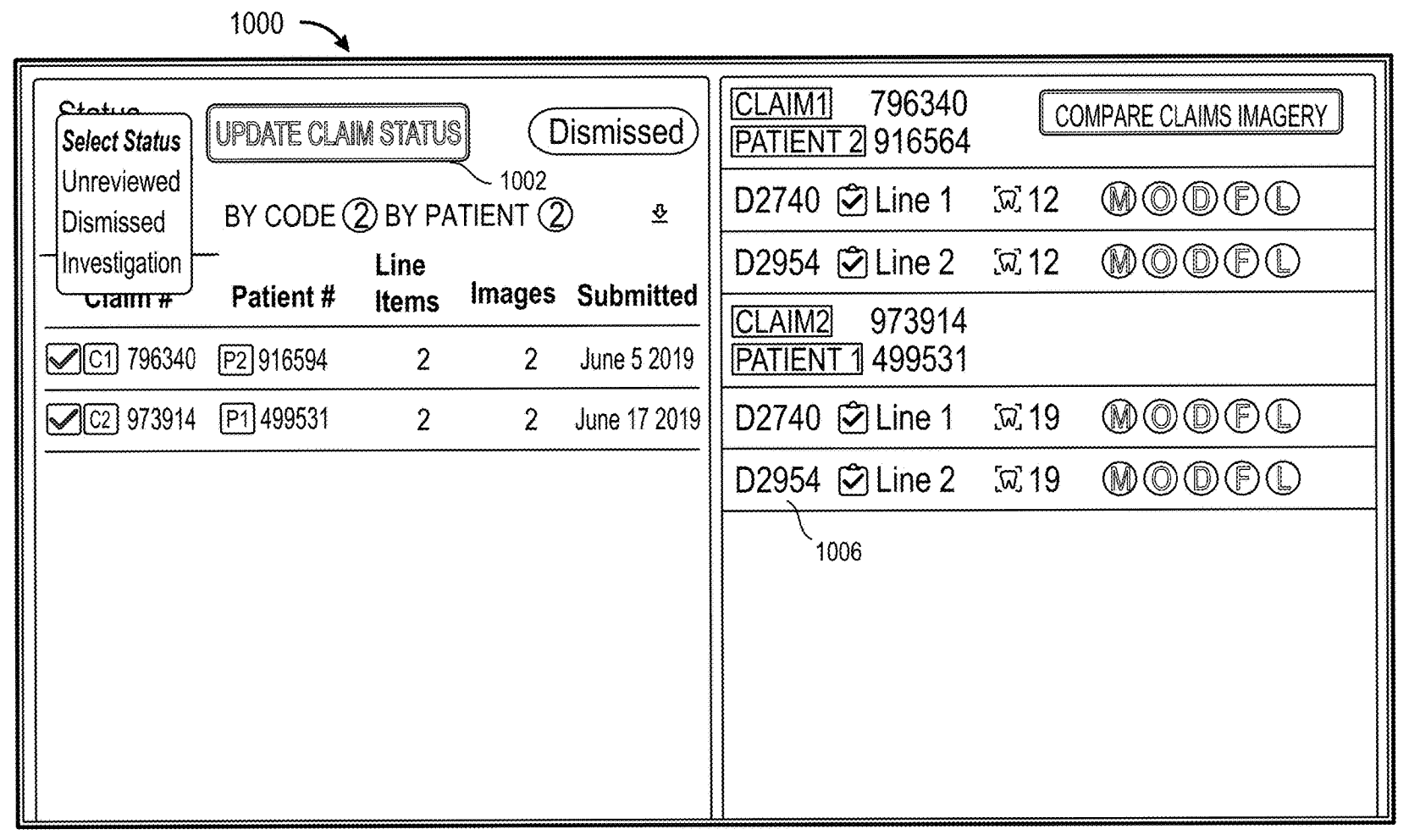
Figure 11:
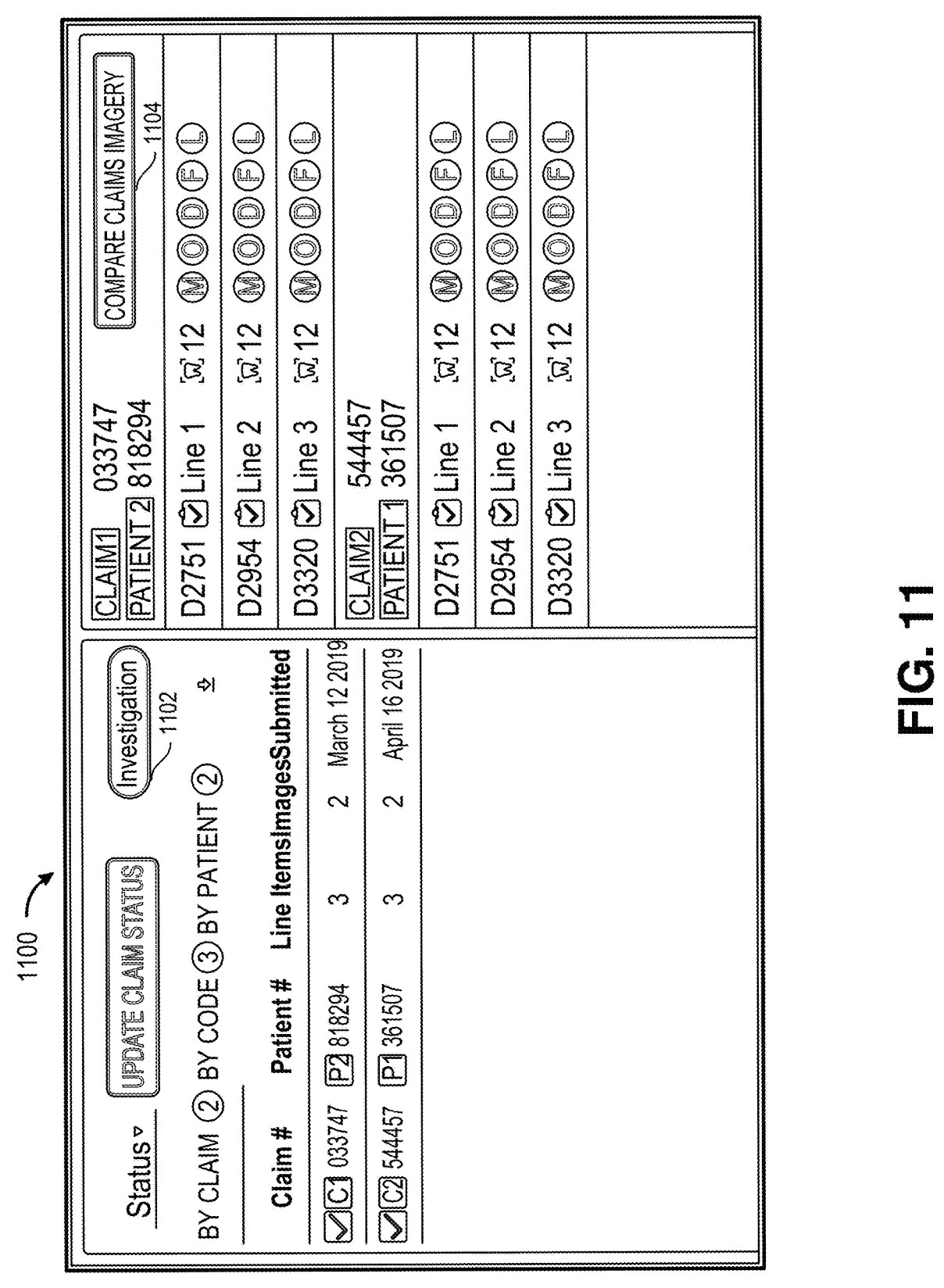

FIGS. 10 and 11 depict illustrative user interfaces 1000 and 1100, respectively, for filtering and reviewing insurance claim information. User interface 1000 includes display of claim information for two claims that are each associated with different patients, identified as "patient 1" and "patient 2," along with corresponding patient identifiers "499531" and "916564"), and which may have been grouped in the same group as each other by the system 120. The group is currently indicated as having status "dismissed," which the user may change by selecting "update claim status" option 1002 (such as to change the status to "investigation" if the user believes that one or both of the claims may be an instance of fraud). Each of the line items for a given claim may be associated with different treatment codes, such as treatment code 1006. Treatment codes (such as D274 and D2954, appearing for both claims in user interface 1000) may be standard dental treatment codes (which may correspond to specific treatments, such as a crown or root canal) submitted to the system 120 as part of the claim information from the carrier.

FIG. 11 depicts a user interface 1100 that is similar to user interface 1000 described above, but for a different claim group, which includes two claims that each have three lines (associated with three separate treatment codes in common between the two claims). As indicated at option 1102, the group has been flagged for further investigation. The user may select "compare claim imagery" option 1104 in order to cause presentation of an updated user interface (which may be in the form of a pop-up window or refreshed interface), such as that shown in FIG. 12, in order to review the similar or matching images that caused the claims to be grouped and flagged.

Figure 12:
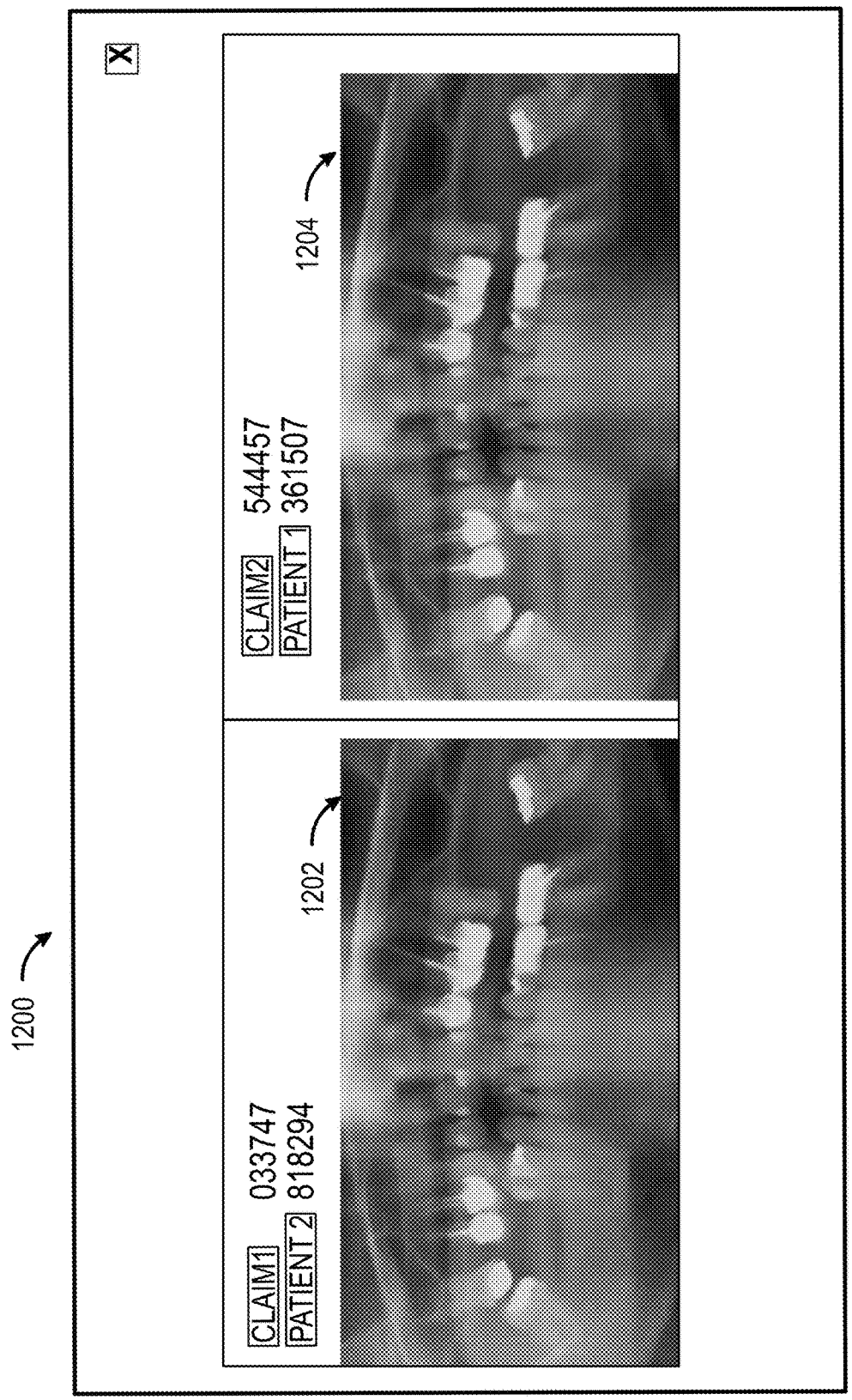
FIG. 12 depicts an illustrative user interface that presents radiographs from two different insurance claim submissions relating to two different patients, where the radiograph images have been flagged according to methods described herein as potential duplicates.

FIG. 12 depicts an illustrative user interface 1200 that presents radiographs from two different insurance claim submissions relating to two different patients, where the radiograph images have been flagged according to methods described herein as potential duplicates. As shown, radiograph images 1202 and 1204 appear identical or nearly identical, but were submitted as supporting evidence for two different insurance claims associated with two different patients. Accordingly, it is likely that at least one of the radiograph images 1202 or 1204 was not in fact a radiograph for the patient that the provider indicated in the given claim submission.

Figure 13:
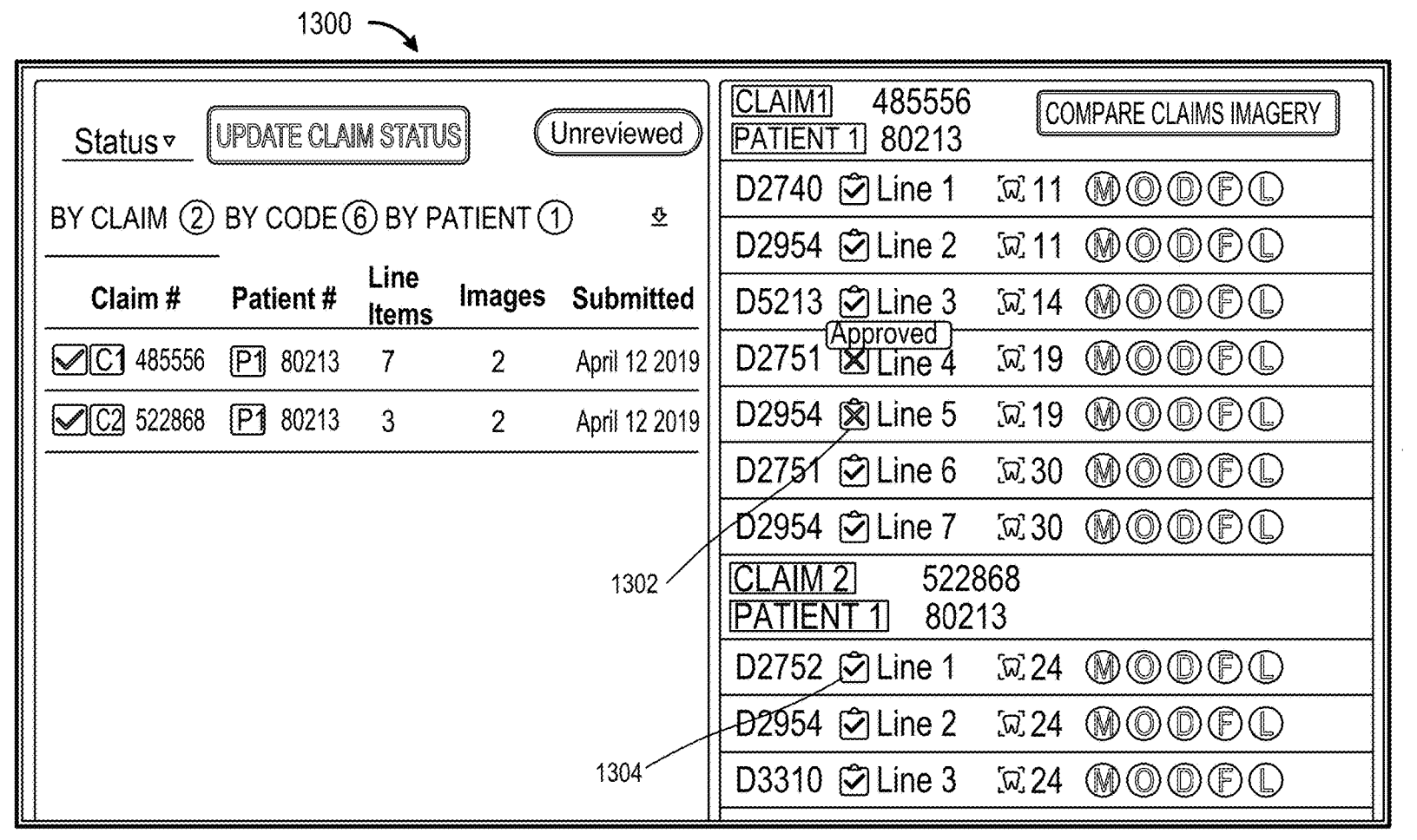

FIG. 13 depicts another illustrative user interface 1300 for reviewing insurance claims. User interface 1300 includes claim information for two claims that relate to the same patient as each other (the patient indicated by patient number "80213"). The data may be historical data for claims that have already been processed by an insurance carrier, but which are being reviewed in an audit process or to check for past fraud. Individual lines of each claim are shown with graphical indicators of whether the given line of the claim was approved or denied by the carrier. For example, the 'X' indicator 1302 may indicate that the carrier denied line 5 of the first claim, while the check indicator 1304 may indicate that the carrier accepted line 1 of the second claim.

Figure 14:
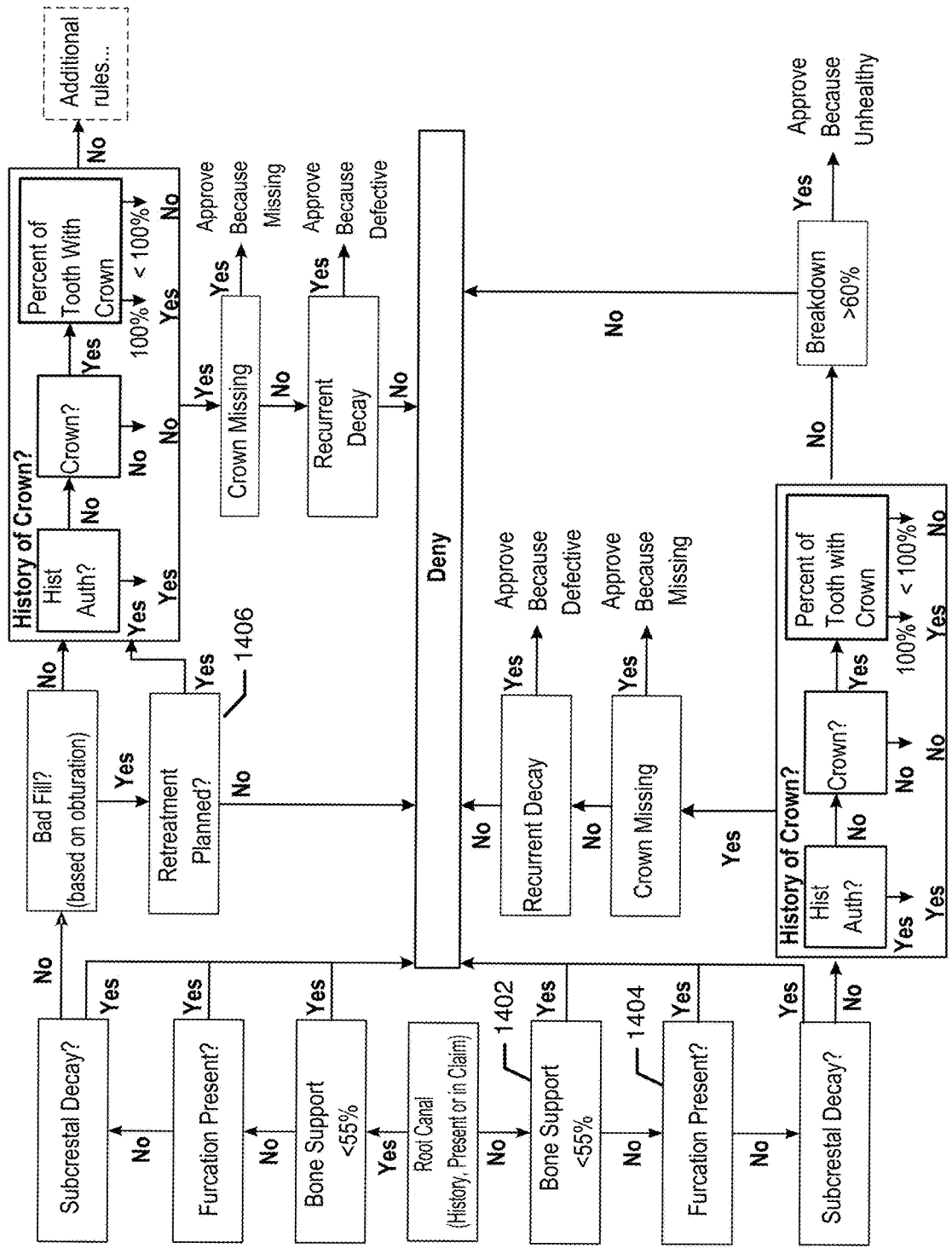
FIG. 14 is an illustrative visual representation of a rule set that may be employed by a system described herein for automatically approving or denying an insurance claim based at least in part on automated review of at least one radiograph image.

FIG. 14 is an illustrative visual representation of a rule set that may be employed by a system described herein for automatically approving or denying an insurance claim (or for flagging a claim for potential approval or denial) based at least in part on automated review of at least one radiograph image. As discussed above, a rule set such as that illustrated in flow chart form in FIG. 14 may be stored in various forms, such as executable code, a JSON or similar format file, an XML file, and/or in other manners. In some embodiments, the insurance claim analysis system 120 may have access to each of a number of different rule sets that are each associated with different insurance carriers and that each indicate carrier-specific rules or heuristics regarding criteria that should be met for approval or denial of claims submitted to the given carrier.

The rule set shown in FIG. 14 may be for a specific carrier to be applied to that carrier's claims, and may have been provided to the system 120 by the carrier or developed by an operator of the system 120 in consultation with the given carrier. As shown in FIG. 14, some individual rules in the rule set may be determined from radiograph image data (such as from output of the machine learning models described above), while others may require consulting a patient's history or other claim information or metadata outside of the supporting image(s) accompanying the claim submission.

For example, a determination such as decision 1402 (whether bone support is less than 55%) and/or decision 1404 (regarding the presence of furcation) may each be automatically determined by the system 120 based on the output of one or more machine learning models provided with image data from a dental radiograph as input. In contrast, decision 1406 (whether retreatment is planned for the patient) may be based on patient data or claim metadata provided to the system 120, and may not be based on the supporting images.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more general purpose computers or processors. The code modules may be stored in any type of non-transitory computer-readable medium or other computer storage device. Some or all the methods may alternatively be embodied in specialized computer hardware. In addition, the components referred to herein may be implemented in hardware, software, firmware or a combination thereof.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A computer system comprising:
one or more electronic data stores that store a plurality of carrier-specific rule sets, wherein each of the carrier-specific rule sets defines claim acceptance criteria for an individual carrier of a plurality of carriers, and wherein the carrier specific rule sets include separate rule sets for at least two different carriers; and a processor in communication with the one or more electronic data stores and configured with processor-executable instructions to perform operations comprising:

obtaining, for a first claim submitted to a first carrier of the plurality of carriers, claim information and at least a first radiograph image associated with the first claim, wherein the first radiograph image has been submitted as supporting evidence of a service indicated in the claim information as having been performed by a submitter of the first claim, wherein the claim information includes a first treatment code associated with the service;

initiating execution of a plurality of machine learning models, wherein input features provided to individual machine learning models of the plurality of machine learning models are based at least in part on image data of the first radiograph image, wherein individual machine learning models of the plurality of machine learning models are trained to detect one or more dental pathologies, anatomies, restorations or anomalies present in the image data;

determining machine learning results based on output of each of the plurality machine learning models, wherein the machine learning results include indication of whether specific ones of the dental pathologies, anatomies, restorations or anomalies are present in the first radiograph image;

retrieving, from among the plurality of carrier-specific rule sets stored in the one or more electronic data stores, a first rule set for the first carrier that includes claim criteria that the first carrier requires be met by claim submissions that include the first treatment code;

based at least in part by applying the first rule set, determining whether the claim information and the machine learning results meet the claim criteria that the first carrier requires be met by claim submissions that include the first treatment code, wherein determining whether the machine learning results meet the claim criteria is based at least in part on a determination of whether a condition indicated in the claim criteria is also indicated in the machine learning results as being present in the first radiograph image, wherein the condition is one of a dental pathology, anatomy, restoration or anomaly;

based at least in part on the determining whether the claim information and the machine learning results meet the claim criteria, determining a confidence score associated with the first claim, wherein the confidence score represents one of (a) confidence that the first claim should be approved by the first carrier or (b) confidence that the first claim is associated with fraud; and based at least in part on the confidence score associated with the first claim, generating at least one of (a) an approval or denial of the first claim, (b) a recommendation to the first carrier to approve or deny the first claim, or (c) user interface data that enables a user to review whether to approve or deny the first claim.

2. The computer system of claim 1, wherein the operations include, based at least in part on the confidence score associated with the first claim, generating the user interface data defining a user interface that enables the user to review whether to approve or deny at least the first claim, wherein the user interface presents information regarding each of two or more claims submitted to the first carrier with corresponding selectable options to view images associated with individual claims of the two or more claims.

3. The computer system of claim 2, wherein the user interface includes an option to group claims based on at least one similarity between images associated with claims of a group.

4. The computer system of claim 2, wherein the user interface includes, for each of the two or more claims, an associated selectable option for the user to flag an individual claim as warranting investigation for potential fraud.

5. The computer system of claim 2, wherein the user interface includes an option to sort a display order of a plurality of claims in the user interface based on associated confidence scores representing whether individual claims are associated with fraud, waste or abuse as determined by the plurality of machine learning models.

6. The computer system of claim 1, wherein the confidence score is further based on comparing a digital signature generated for the first radiograph image to previously generated digital signatures of other images that have been submitted in association with claims other than the first claim.

7. The computer system of claim 6, wherein the processor is further configured to generate the digital signature for the first radiograph image, wherein the digital signature for the first radiograph image is generated at least in part by:

extracting a plurality of features from image data of the first radiograph image; and applying a hashing function to at least a subset of the plurality of features to generate the digital signature.

8. The computer system of claim 6, wherein the comparing of the digital signature generated for the first radiograph image to the previously generated digital signatures results in a determination that the digital signature matches a previous digital signature associated with an image from a second claim submitted to the computer system prior to the first claim, wherein the operations further comprise:

determining that the first claim is associated with potential fraud based at least in part on the comparing of the digital signature generated for the first radiograph image to the previously generated digital signatures indicating that a radiograph depicted in the first radiograph image is not a radiograph first captured in association with the first claim.

9. The computer system of claim 1, wherein the computer system implements an application programming interface (API) configured to receive requests from each of the plurality of carriers, wherein the claim information for the first claim is obtained by the computer system from a computing device associated with the first carrier via the API.

10. A computer-implemented method comprising:

as implemented by one or more computing devices configured with specific executable instructions, obtaining, for a first claim submitted to a first carrier, claim information and at least a first radiograph image associated with the first claim, wherein the first radiograph image has been submitted as supporting evidence of a service indicated in the claim information as having been performed by a submitter of the first claim, wherein the claim information includes a first treatment code associated with the service;

initiating execution of a plurality of machine learning models, wherein input features provided to individual machine learning models of the plurality of machine learning models are based at least in part on image data of the first radiograph image, wherein individual machine learning models of the plurality of machine learning models are trained to detect one or more dental pathologies, anatomies, restorations or anomalies present in the image data;

determining machine learning results based on output of each of the plurality machine learning models, wherein the machine learning results include indication of whether specific ones of the dental pathologies, anatomies, restorations or anomalies are present in the first radiograph image;

retrieving a first rule set for the first carrier that includes claim criteria that the first carrier requires be met by claim submissions that include the first treatment code;

based at least in part by applying the first rule set, determining whether the claim information and the machine learning results meet the claim criteria that the first carrier requires be met by claim submissions that include the first treatment code, wherein determining whether the machine learning results meet the claim criteria is based at least in part on a determination of whether a condition indicated in the claim criteria is also indicated in the machine learning results as being present in the first radiograph image, wherein the condition is one of a dental pathology, anatomy, restoration or anomaly;

based at least in part on the determining whether the claim information and the machine learning results meet the claim criteria, determining a confidence score associated with the first claim, wherein the confidence score represents one of (a) confidence that the first claim should be approved by the first carrier or (b) confidence that the first claim is associated with fraud; and based at least in part on the confidence score associated with the first claim, generating at least one of (a) an approval or denial of the first claim, (b) a recommendation to the first carrier to approve or deny the first claim, or (c) user interface data that enables a user to review whether to approve or deny the first claim.

11. The computer-implemented method of claim 10, wherein the first rule set includes both (a) a first rule that applies to results of an automated image analysis of a radiograph and (b) a second rule that applies to patient history data.

12. The computer-implemented method of claim 10 further comprising extracting the first image and a plurality of additional images associated with the first claim from a composite image submitted by a healthcare provider as supporting evidence for the first claim.

13. The computer-implemented method of claim 10, wherein a subset of the plurality of machine learning models comprise ensemble detectors that are collectively configured to predict presence of a plurality of dental pathologies in an image.

14. The computer-implemented method of claim 10, wherein the plurality of machine learning models include at least two different types of convolutional neural networks that are each trained to identify a different dental pathology.

15. The computer-implemented method of claim 10 further comprising:
determining that the confidence score meets an approval threshold; and based on the confidence score meeting the approval threshold, sending, via an application programming interface (API) to a computing system associated with the first carrier, an indication or recommendation that the first claim be approved by the first carrier.

16. The computer-implemented method of claim 10 further comprising:
determining that the confidence score meets a denial threshold; and based on the confidence score meeting the denial threshold, sending, via an application programming interface (API) to a computing system associated with the first carrier, an indication or recommendation that the first claim be denied by the first carrier.

17. A computer-readable, non-transitory storage medium storing computer executable instructions that, when executed by one or more computer systems, configure the one or more computer systems to perform operations comprising:

obtaining, for a first claim submitted to a first carrier, claim information and at least a first radiograph image associated with the first claim, wherein the first radiograph image has been submitted as supporting evidence of a service indicated in the claim information as having been performed by a submitter of the first claim, wherein the claim information includes a first treatment code associated with the service;

initiating execution of a plurality of machine learning models, wherein input features provided to individual machine learning models of the plurality of machine learning models are based at least in part on image data of the first radiograph image, wherein individual machine learning models of the plurality of machine learning models are trained to detect one or more dental pathologies, anatomies, restorations or anomalies present in the image data;

determining machine learning results based on output of each of the plurality machine learning models, wherein the machine learning results include indication of whether specific ones of the dental pathologies, anatomies, restorations or anomalies are present in the first radiograph image;

retrieving a first rule set for the first carrier that includes claim criteria that the first carrier requires be met by claim submissions that include the first treatment code;

based at least in part by applying the first rule set, determining whether the claim information and the machine learning results meet the claim criteria that the first carrier requires be met by claim submissions that include the first treatment code, wherein determining whether the machine learning results meet the claim criteria is based at least in part on a determination of whether a condition indicated in the claim criteria is also indicated in the machine learning results as being present in the first radiograph image, wherein the condition is one of a dental pathology, anatomy, restoration or anomaly;

based at least in part on the determining whether the claim information and the machine learning results meet the claim criteria, determining a confidence score associated with the first claim, wherein the confidence score represents one of (a) confidence that the first claim should be approved by the first carrier or (b) confidence that the first claim is associated with fraud; and based at least in part on the confidence score associated with the first claim, generating at least one of (a) an approval or denial of the first claim, or (b) user interface data for presentation to the first carrier indicating whether the first claim is associated with potential fraud.

18. The computer-readable, non-transitory storage medium of claim 17, wherein the operations further comprise generating a user interface for presentation to the first carrier, wherein the user interface includes information identifying each of a plurality of claims, wherein at least a subset of the plurality of claims are presented in the user interface with a visual indicator of potential fraud as determined from digital signature comparisons of images from two or more claims.

19. The computer-readable, non-transitory storage medium of claim 18, wherein the at least a subset of the plurality of claims are further presented in the user interface with corresponding selectable options for a user to indicate approval or denial of individual claims presented in association with the visual indicator of potential fraud.

\* \* \* \* \*